United States Patent
Chen et al.

(10) Patent No.: US 10,562,864 B2
(45) Date of Patent: Feb. 18, 2020

(54) CHEMICAL MODULATORS OF IMMUNE CHECKPOINTS AND THERAPEUTIC USE

(71) Applicant: Duke University, Durham, NC (US)

(72) Inventors: Wei Chen, Chapel Hill, NC (US); Herbert Kim Lyerly, Chapel Hill, NC (US); Xiu-rong Ren, Durham, NC (US); Jiangbo Wang, Durham, NC (US); Hongtao Guo, Durham, NC (US); Amy Hobeika, Durham, NC (US); Robert A. Mook, Jr., Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/191,243

(22) Filed: Nov. 14, 2018

(65) Prior Publication Data

US 2019/0077772 A1  Mar. 14, 2019

Related U.S. Application Data

(63) Continuation of application No. 15/395,464, filed on Dec. 30, 2016, now Pat. No. 10,189,797, which is a continuation of application No. 62/272,859, filed on Dec. 30, 2015.

(51) Int. Cl.
| | |
|---|---|
| *C07D 249/08* | (2006.01) |
| *C07D 235/18* | (2006.01) |
| *A61K 31/4196* | (2006.01) |
| *A61K 31/4184* | (2006.01) |
| *A61K 45/06* | (2006.01) |

(52) U.S. Cl.
CPC ........ *C07D 249/08* (2013.01); *A61K 31/4184* (2013.01); *A61K 31/4196* (2013.01); *A61K 45/06* (2013.01); *C07D 235/18* (2013.01)

(58) Field of Classification Search
CPC .......................... C07D 249/08; C07D 235/18; A61K 31/4196; A61K 31/4184; A61K 45/06
See application file for complete search history.

(56) References Cited

U.S. PATENT DOCUMENTS 6,469,058 B1  10/2002  Grove et al.

OTHER PUBLICATIONS

Ansel, "Introduction to Pharmaceutical Dosage Forms," 2nd ed., 1976, Lea & Febiger, Philadelphia.
Banker et al., "Modern Pharmaceutics," 1979, Marcel Dekker, Inc., New York, chapters 9 and 10.
Blank et al., "PD-L1/B7H-1 Inhibits the Effector Phase of Tumor Rejection by T Cell Receptor (TCR) Transgenic CD8+ T Cells," Cancer Research, 2004, 64(3):1140-1145.
Burns, "McCutcheon's Volume 1: Emulsifiers & Detergents," North American ed., 1994, MC Publishing Co., Glen Rock, pp. 236-239.
Carruthers, "Some Modem Methods of Organic Synthesis," 3rd ed., 1987, Cambridge University Press, Cambridge.
Furniss et al., "Vogel's Textbook of Practical Organic Chemistry", 5th ed., 1989, Longman Scientific & Technical, Essex.
Gennaro et al., "Remington's Pharmaceutical Sciences," 15th ed., 1975, Mack Publishing Co., Easton, pp. 335-337.
Guo, et al., "Enantioselective addition of diethylzinc to benzaldehyde catalyzed by chiral titanate complexes with helical ligands," Tetrahedron, 1997, 53(12):4145-4158.
International Union of Pure and Applied Chemistry, "Rules for the Nomenclature of Organic Chemistry, Section E: Stereochemistry," Pure Appl. Chem., 1976, 45(1):13-30.
Iwai et al., "Involvement of PD-L1 on tumor cells in the escape from host immune system and tumor immunotherapy by PD-L1 blockade," PNAS, 2002, 99(19):12293-12297.
Larock, "Comprehensive Organic Transformations," 2nd ed., 1989, VCH Publishers, Inc., New York.
Lieberman et al., "Pharmaceutical Dosage Forms: Tablets," 2nd ed., 1981, Marcel Dekker, Inc., New York.
Niu et al., "An in silico protocol for identifying potential poly(ADP-ribose)polymerase-1 (PARP-1) inhibitors from chemical databases," New Journal of Chemistry, 2015, 39:1060-1066.
Ohigashi et al., "Clinical significance of programmed death-1 ligand-1 and programmed death-1 ligand-2 expression in human esophageal cancer," Clinical Cancer Research, 2005, 11(8):2947-2953.
Porichis et al., "Role of PD-1 in HIV pathogenesis and as target for therapy," Current HIV/AIDS Reports, 2012, 9(1):81-90.
Said et al., "Programmed death-1-induced interleukin-10 production by monocytes impairs CD4+ T cell activation during HIV infection.," Nature Medicine, 2010, 16(4):452-459.
Smith et al., "March's Advanced Organic Chemistry," 5th ed., 2001, John Wiley & Sons, Inc., New York.
Sorrell, "Organic Chemistry," 2nd ed., 1999, University Science Books, Sausalito.
Topalian et al., "Safety, Activity, and Immune Correlates of Anti-PD-1 Antibody in Cancer," The New England Journal of Medicine, 2012, 366(26):2443-54.
Velu et al., "Role of PD-1 co-inhibitory pathway in HIV infection and potential therapeutic options," Retrovirology, 2015, 12:14.
Wenninger et al., "C.T.F.A. Cosmetic Ingredient Handbook," 2nd ed., 1992, Cosmetic, Toiletry, and Fragrance Association, Washington D.C., pp. 587-592.
Wuts et al., "Greene's Protective Groups in Organic Synthesis," 4th ed., 2006, John Wiley & Sons, Inc., New York.

*Primary Examiner* — Sahar Javanmard
(74) *Attorney, Agent, or Firm* — Michael Best & Friedrich LLP

(57) ABSTRACT

Compounds and pharmaceutical compositions that down-regulate immune checkpoints such as PD-1, PD-L1 and CTLA-4 are provided. Also provided are methods of treating a disease by down-regulating immune checkpoints such as PD-1, PD-L1 and CTLA-4. The methods are useful for treating cancer and viral infection in a subject.

4 Claims, 13 Drawing Sheets

CHEMICAL MODULATORS OF IMMUNE CHECKPOINTS AND THERAPEUTIC USE

CROSS-REFERENCE TO RELATED APPLICATION

This application is a continuation of U.S. patent application Ser. No. 15/395,464, filed Dec. 30, 2016, which application claims the benefit of and priority to U.S. Provisional Application No. 62/272,859, filed on Dec. 30, 2015, the content of which are incorporated by reference herein in their entirety, and priority to which is hereby claimed.

STATEMENT OF GOVERNMENT INTEREST

This invention was made with government support under Grant numbers R01-CA172570 awarded by the National Cancer Institute (NCI); 5K12-CA100639-08 awarded by the National Cancer Institute (NCI); and BC 123280 awarded by the Department of Defense (DOD). The government has certain rights in the invention.

TECHNICAL FIELD

The present disclosure relates to compounds, compositions, and methods for down-regulating immune checkpoints (e.g., PD-1, PD-L1, CTLA-4) and treating diseases, disorders or conditions associated with immune checkpoints.

BACKGROUND

Immune checkpoint therapy, which targets regulatory pathways in T cells to enhance antitumor immune responses, has led to important clinical advances and provides a new weapon against cancer. This therapy has elicited durable clinical responses and, in a fraction of patients, long-term remissions where patients exhibit no clinical signs of cancer for many years.

A number of these immune checkpoints, such as CTLA-4 (cytotoxic T-lymphocyte antigen 4), and PD-1 (programmed death 1) are known to prevent T cells from attacking tumor cells. Therapies comprising antibodies that target CTLA-4 (e.g., ipilimumab) and PD-1 (e.g., nivolumab and pembrolizumab) are known to boost the immune response against cancer cells and have shown efficacy in treating certain cancers. However, the cost and required route of administration (IV), coupled with deleterious side effects, are a hurdle to patient compliance.

Accordingly, there exists a need for small molecules that target and down-regulate immune checkpoints that are appropriate for oral dosing to subjects in need of anticancer therapy.

SUMMARY OF THE INVENTION

In one aspect, disclosed is a method of treating cancer in a subject in need thereof, the method comprising administering to the subject an effective amount of a compound of formula (I), or a pharmaceutically acceptable salt thereof,

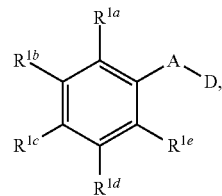

(I)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together form a ring; A is heteroaryl; D is hydrogen, halogen, nitro, alkyl, cyano, haloalkyl, aryl or heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl —C(O)—NH-alkyl, and —C(O)-heterocycle; $R^5$, $R^6$ and $R^7$ are each independently selected from hydrogen, alkyl, —C(O)-alkyl, —C(O)-alkoxyalkyl, alkenyl, alkynyl, and heteroalkyl; $R^8$ is selected from hydrogen and alkyl; and $R^9$ is selected from hydrogen, alkyl, aryl, heteroaryl, arylalkyl, heterocycle, and heteroarylalkyl.

In another aspect, disclosed is a method of treating cancer in a subject in need thereof, the method comprising administering to the subject an effective amount of a compound of formula (II), or a pharmaceutically acceptable salt thereof,

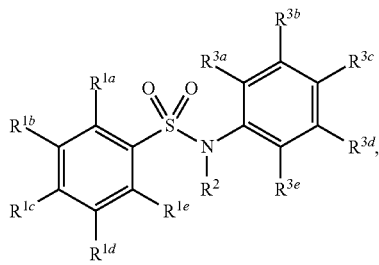

(II)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together form a ring; $R^2$ is selected from hydrogen, alkyl, —C(O)-alkyl, and —C(O)-alkenyl, or $R^2$ and $R^{1e}$ together form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, $SO_2$—$R^9$ and $NR^8$—$SO_2$—$R^9$; $R^4$ is selected from hydrogen, alkyl, —C(O)-alkyl, —C(O)-alkenyl, C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, —C(O)—O-alkoxyalkyl, —C(O)—NH-alkyl, and —C(O)-heterocycle; $R^5$, $R^6$ and $R^7$ are each independently selected from hydrogen, alkyl, —C(O)-alkyl, —C(O)-alkenyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl.

In another aspect, disclosed is a method of treating a disease associated with dysregulation of the Wnt/Frizzled signaling pathway in a subject in need thereof, the method comprising administering to the subject an effective amount of a compound of formula (III), or a pharmaceutically acceptable salt thereof,

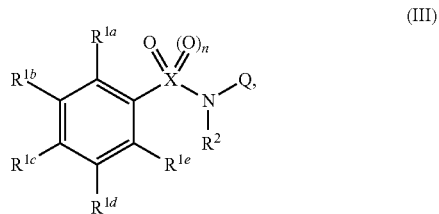

(III)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together form a ring; X is C or S; n is 0 or 1; $R^2$ is selected from hydrogen, alkyl, —C(O)-alkyl, and —C(O)-alkenyl, or $R^2$ and $R^{1e}$ together form a ring; Q is heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl —C(O)—NH-alkyl, and —C(O)-heterocycle; $R^5$, $R^6$ and $R^7$ are each independently selected from hydrogen, alkyl, —C(O)-alkyl, —C(O)-alkoxyalkyl, alkenyl, alkynyl, and heteroalkyl; $R^8$ is selected from hydrogen and alkyl; and $R^9$ is selected from hydrogen, alkyl, aryl, heteroaryl, arylalkyl, heterocycle, and heteroarylalkyl.

In another aspect, disclosed is a method of treating cancer in a subject in need thereof, the method comprising administering to the subject an effective amount of a compound selected from the group consisting of: 4-chloro-2-((2-chloro-4-nitrophenyl)carbamoyl)phenyl octanoate; 6-chloro-2-(trifluoromethyl)-N-(4-(trifluoromethyl)phenyl)-1H-benzo[d]imidazole-4-carboxamide; 5-chloro-N-(2-chloro-4-(trifluoromethyl)phenyl)-2-hydroxybenzamide; 5-chloro-N-(3,5-dichlorophenyl)-2-hydroxybenzamide; 5-bromo-2-((4-methylphenyl)sulfonamido)-N-(4-(trifluoromethyl)phenyl)benzamide; and (2-butylbenzofuran-3-yl)(4-(2-(diethylamino)ethoxy)-3,5-diiodophenyl)methanone, or a pharmaceutically acceptable salt thereof.

In another aspect, disclosed are methods for down-regulating an immune checkpoint in a subject in need thereof, the method comprising administering to the subject an effective amount of a compound disclosed herein or a pharmaceutically acceptable salt thereof to a subject in need thereof.

In another aspect, disclosed are pharmaceutical compositions comprising at least one pharmaceutically acceptable carrier and an effective amount of a compound disclosed herein.

Other aspects of the disclosure include methods of treating other diseases, disorders or conditions (e.g., viral infections) that may be treated by down-regulating immune checkpoints.

DETAILED DESCRIPTION

Figure 1:
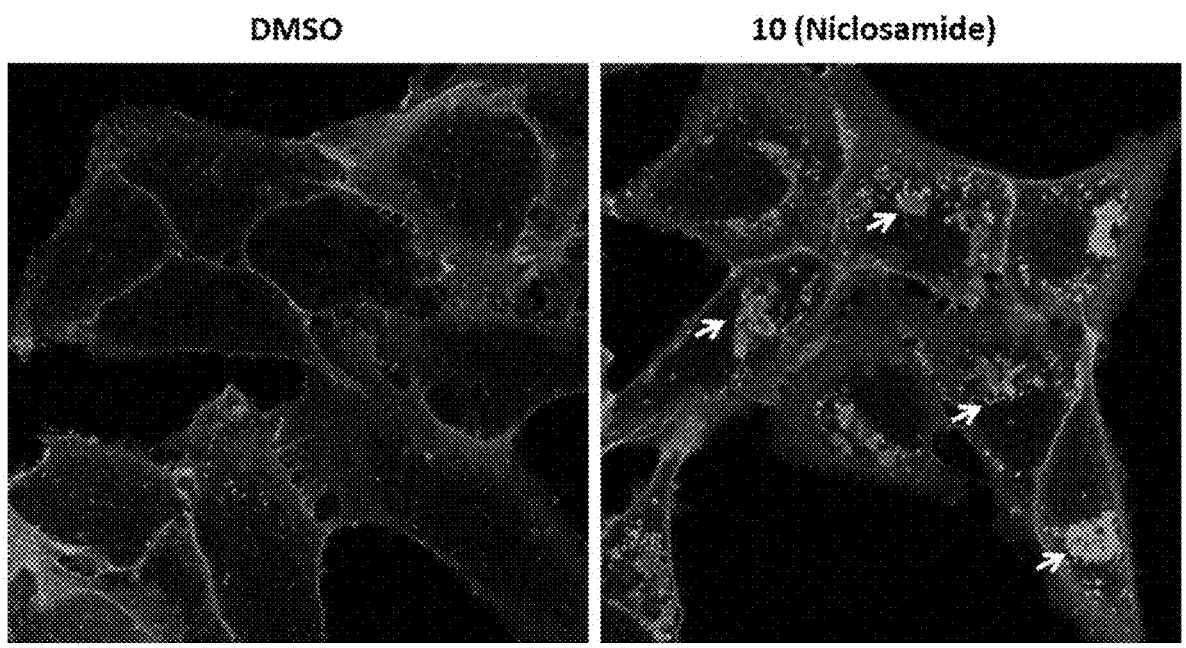
FIG. 1 shows confocal images of PD1-GFP stable U2OS cells treated with DMSO control or niclosamide (10 μM) for 6 h at 37° C. Punctuate and aggregate structures (white arrows) highlight internalized PD1-GFP vesicles.

Disclosed herein are compounds for and methods of treating cancer by way of down-regulating immune checkpoints such as PD-1, PD ligand 1 (PD-L1) and CTLA-4. The compounds disclosed herein stimulate internalization of the checkpoint proteins and decrease protein levels to down-regulate the activity of the immune checkpoints. Accordingly, the compounds disclosed herein may serve as a blockade to the described immune checkpoints and allow T-cells to attack cancerous cells and tumors, and thus providing valuable therapeutic anticancer agents and methods.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "effective amount," as used herein, refers to a dosage of the compounds or compositions effective for eliciting a desired effect. This term as used herein may also refer to an amount effective at bringing about a desired in vivo effect in an animal, preferably, a human, such as treatment of a disease.

The term "treatment", as used herein in the context of treating a condition, pertains generally to treatment and therapy, whether of a human or an animal (e.g. in veterinary applications), in which a desired therapeutic effect is achieved. For example, treatment includes prophylaxis and can ameliorate or remedy the condition, disease, or symptom, or treatment can inhibit the progress of the condition or disease (e.g., reduce the rate of disease/symptom progression or halt the rate of disease/symptom progression).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "alkoxy" as used herein, means at least one alkyl group, as defined herein, is appended to the parent molecular moiety through an oxygen atom. Representative examples of alkoxy include, but are not limited to, methoxy, ethoxy, and isopropoxy.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "carboxyl" as used herein, means a carboxylic acid, or —COOH.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" as used herein, means Cl, Br, I, or F.

The term "heteroalkyl," as used herein, means an alkyl group, as defined herein, in which at least one of the carbons of the alkyl group is replaced with a heteroatom, such as oxygen, nitrogen, and sulfur.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo [2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), and oxa-adamantane (2-oxatricyclo[3.3.1.1$^{3,7}$] decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclealkyl" as used herein, refers to a heterocycle group, as defined herein, appended to the parent molecular moiety through an alkylene group, as defined herein.

The term "hydroxyl" or "hydroxy" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated

2. METHODS OF TREATMENT

The disclosed compounds and compositions may be used in methods for treatment of cancer. The disclosed compounds and compositions may be used in methods for treatment of viral infections. The methods of treatment may comprise administering to a subject in need of such treatment a composition comprising an effective amount of the compound of formula (I), the compound of formula (II), the compound of formula (III) or any compound disclosed herein.

The compositions can be administered to a subject in need thereof to down-regulate immune checkpoints such as PD-1, PD-L1 and CTLA-4 for a variety of diverse biological processes. As such, the present disclosure is directed to methods of administering the compositions to down-regulate immune checkpoints and promote certain immune responses (e.g., T-cells) that may attack and destroy cancerous cells and tumors. Accordingly, the disclosed compounds and compositions may be administered to a subject for the treatment of a variety of cancer types.

The compositions may be useful for treating and preventing certain cancers in humans and animals. Treatment or prevention of such cancers can be effected by down-regulating immune checkpoints in a subject, by administering a compound or composition of the disclosure, either alone or in combination with another active agent as part of a therapeutic regimen to a subject in need thereof.

In certain embodiments, provided are methods of identifying a subject with a cancer that may be amenable to treatment by a disclosed method. For example, a subject may be identified with a cancer that is particularly susceptible to treatment by down-regulation of immune checkpoints.

a. Cancer

Down-regulation of immune checkpoints (e.g., PD-1, PD-L1 and CTLA-4) can lead to treatment and reduction of cancer or tumor growth, and/or reduce metastasis of cancerous or tumor cells. Accordingly, the disclosed compositions can be used in methods that treat and/or prevent cancer or tumors in a subject administered the compound. The method can treat cancer or tumor based growth and can be any type of cancer such as, but not limited to, melanoma, lymphoma, pancreatic cancer, multiple myeloma, prostate cancer, renal cell carcinoma, bladder cancer, non-small cell lung cancer, esophageal cancer, gastric cancer, colon cancer, liver cancer, ovarian cancer, breast cancer, or a combination thereof.

In some embodiments, the administered composition to a subject in need thereof can mediate reduction, clearance or prevention of additional growth of tumor cells by down-regulating the immune checkpoints (e.g., PD-1, PD-L1 and CTLA-4), thereby reducing growth/proliferation or modifying differentiation of tumor cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

1. PD-1/PD-L1

Programmed cell death protein 1, (PD-1) is a protein that, in humans, is encoded by the PDCD1 gene. PD-1 is a cell surface receptor that belongs to the immunoglobulin superfamily and is expressed on T cells and pro-B cells. PD-1 binds two ligands, PD-L1 and PD-L2. PD-1, functioning as an immune checkpoint, plays an important role in down-regulating the immune system by preventing the activation of T-cells, which in turn reduces autoimmunity and promotes self-tolerance. The inhibitory effect of PD-1 is accomplished through a dual mechanism of promoting apoptosis in antigen specific T-cells in lymph nodes while simultaneously reducing apoptosis in regulatory T cells (suppressor T cells).

PD-1 has been explored as a target for immunotherapy due to its ability to activate the immune system to attack tumors. Specifically, the 2C T-cell receptor (TCR) recognizes the peptide SIYRYYGL in the context of H 2 kb. 2C CD8 T cells incubated with IFN-$\gamma$ treated B16 targets expressing SIYRYYGL peptide poorly lyse their targets and secrete low levels of IL-2. However, PD-1 knockout 2C T cells have heightened cytolytic capacity and IL-2 secretion, suggesting that PD-1 negatively regulates anti-tumor CD8 T cell responses. Similarly, P815 mastocytoma, which does not express PD-L1 unless treated with IFN-$\gamma$, can be transduced to express PD-L1, resulting in inhibition of in vitro CD8-mediated cytotoxicity and enhanced in vivo tumor growth. In vitro cytotoxicity and in vivo inhibition of growth can be restored by anti-PD-L1 antibodies or by genetic ablation of PD-1 (Iwai et al. *PNAS*, 2002, 99(19). 12293-7; Blank et al. *Cancer Research*, 2004, 64 (3), 1140-5). These data suggest that expression of PD-L1 on tumor cells inhibits anti-tumor activity through engagement of PD-1 on effector T cells. Expression of PD-L1 on tumors is correlated with reduced survival in esophageal, pancreatic and other types of cancers, highlighting this pathway as a target for immunotherapy (Ohigashi et al. *Clinical Cancer Research*, 2005, 11(8), 2947-53). Further studies (Said et al. *Nature Medicine*, 2010, 16 (4): 452-9) show that triggering PD-1, expressed on monocytes and up-regulated upon monocytes activation, by its ligand PD-L1 induces IL-10 production, which inhibits CD4 T-cell function.

Monoclonal antibodies targeting PD-1 that boost the immune system have been developed for the treatment of cancer by forming an immune checkpoint blockade. Many tumor cells express PD-L1, an immunosuppressive PD-1 ligand, and inhibition of the interaction between PD-1 and PD-L1 can enhance T-cell responses in vitro and mediate preclinical antitumor activity.

Nivolumab, an anti-PD-1 antibody drug, produced complete or partial responses in non-small-cell lung cancer, melanoma, and renal-cell cancer, in a clinical trial (Topalian et al. *The New England Journal of Medicine,* 2012, 366 (26), 2443-54), and was approved by the FDA to treat metastatic melanoma.

Pembrolizumab, which also targets PD-1 receptors, was approved by the FDA to treat metastatic melanoma and advanced (metastatic) non-small cell lung cancer (NSCLC) patients. Other drugs in early stage development targeting PD-1 receptors include pidilizumab, BMS 936559 and MPDL328OA.

2. CTLA-4

The CTLA-4 (cytotoxic T-lymphocyte-associated protein 4) protein is encoded by the CTLA-4 gene in humans. CTLA-4 is a protein receptor that, functioning as an immune checkpoint, down-regulates the immune system. CTLA-4 is found on the surface of T cells, and acts as an "off" switch when bound to CD80 or CD86 on the surface of antigen-presenting cells.

Intracellular CTLA-4 is also found in regulatory T cells and may be important to their function. T cell activation through the T cell receptor and CD28 leads to increased expression of CTLA-4, an inhibitory receptor for B7 molecules.

The therapeutic benefits of blocking CTLA-4 have been shown recently. Antagonistic antibodies against CTLA-4 such as ipilimumab (approved by the FDA for treatment of melanoma) are a means of inhibiting immune system tolerance to tumors and thereby providing a potentially useful immunotherapy strategy for patients with cancer. Ipilimumab is the first approved immune checkpoint blockade therapy.

Accordingly, the foregoing firmly establish the down-regulation of immune checkpoints PD-1, PD-L1 and CTLA-4 as a viable treatment of a variety of cancer types.

b. Viral Infections

Drugs targeting PD-1 may augment immune responses and/or facilitate HIV eradication (Porichis et al. *Current HIV/AIDS Reports* 2012, 9(1). 81-90). In recent years, studies in mice and non-human primate models of HIV infection have demonstrated that the functional exhaustion of virus-specific T and B cells could be reversed by blockade of interaction between PD-1 and PD-L1. Recent advances in the understanding of the PD-1 pathway in HIV/SIV infection have led to investigation into the beneficial effects of PD-1 blockade during chronic HIV/SIV infection and its potential role as immunotherapy for HIV/AIDS. Therapy directed at PD-1 also has a significant advantage to control chronic infections such as HCV and HBV. (Velu et al. *Retrovirology,* 2015, 12:14).

c. Modes of Administration

Methods of treatment may include any number of modes of administering a disclosed composition. Modes of administration may include tablets, pills, dragées, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

d. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present disclosure. The above combinations include combinations of a compound of the present disclosure not only with one other active compound, but also with two or more other active compounds. For example, the compound of the disclosure can be combined with a variety of anti-cancer drugs and chemotherapeutics.

The disclosed compounds can be combined with the following, but not limited to, actinomycins, alkylating agents, anthracyclines, antifolates, antiestrogen agents, antimetabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multidrug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs. Specific anti-cancer or chemotherapeutic agents that may be combined with a disclosed compound include actinomycin D, AG13736, alisertib, 17-allylamino-17-demethoxygeldanamycin, altretamine, 9-aminocamptothecin, N-(4-(3-amino-1H-indazol-4-yl)phenyl}-N'-(2-fluoro-5-methylphenyl) urea, N-(4-(4-aminothieno[2,3-d]pyrimidin-5-yl)phenyl}-

N'-(2-fluoro-5-(trifluoromethyl)phenyl)urea, anastozole, AP-23573, asparaginase, axitinib, azacitidine, bevacizurnab, bicalutamide, bevacizumab, bleomycin a2, bleomycin b2, bortezemib, busulfan, campathecins, carboplatin, carmustine (BCNU), CB1093, CHOP (C: Cytoxan® (cyclophosphamide); H: Adriamycin® (hydroxydoxorubicin); O: Vincristine (Oncovin®); P: prednisone), chlorambucil, CHIR258, cilengitide, cisplatin, CNF-101, CNF-1001, CNF-2024, CP547632, crisnatol, cytarabine, cyclophosphamide, cytosine arabinoside, daunorubicin, dabrafenib, dacarbazine, dactinomycin, dasatinib, daunorubicin, deferoxamine, demethoxyhypocrellin A, depsipeptide, 17-dimethylaminoethylamino-17-demethoxygeldanamycin, docetaxel, doxifluridine, doxorubicin, EB 1089, enzastaurin, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzene-sulfonamide, hydroxyurea, idarubicin, ifosfamide, imatinab, ipilimumab, interferon-α, interferon-γ, IPI-504, irinotecan, KH 1060, lapatinib, leucovorin calcium, LAQ824, leuprolide acetate, letrozole, lomustine (CCNU), melphalan, mercaptopurine, methotrexate, 1-methyl-4-phyenylpyridinium, MG132, mitoxantrone, mitozolomide, MLN4924, MLN518, MS-275, mycophenolic acid, nedaplatin, oprelvekin, oxaliplatin, paclitaxel, panitumumab, PD98059, pazopanib, pembrolizumab, peplomycin, phtalocyanine, pirarubicin, plicamycin, procarbazine, PTK787, PU24FC1, PU3, radicicol, raloxifene, rapamycin, ratitrexed, pheuretinide, ribavirin, rituximab (Rituxin®), satraplatin, sorafenib, staurosporine, suberoylanilide hydroxamic acid, sunitinib, tamoxifen, taxol, temozolomide, temsirolimus, teniposide, thapsigargin, thioguanine, thrombospondin-1, tiazofurin, topotecan, trapoxin, treosulfan, trichostatin A, trimetrexate, triplatin tetranitrate, trofosfamide, tumor necrosis factor, valproic acid, vemurafenib, VER49009, verapamil, vertoporfin, vinblastine, vincristine, vindesine, vinorelbine vitamin D3, VX-680, zactima, ZK-EPO, zorubicin, trastuzumab, cetuximab, lambrolizumab, nivolumab, pidilizumab, BMS 936559, and MPDL328OA, or any combination thereof.

The disclosed compounds may be included in kits comprising the compound [e.g., one or more disclosed compound], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

3. COMPOUNDS

In one aspect, disclosed is a compound of formula (I):

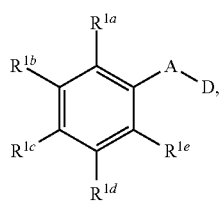

(I)

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together with the atoms to which they are attached form a ring; A is heteroaryl; D is hydrogen, halogen, nitro, alkyl, cyano, haloalkyl, cycloalkyl, aryl or heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl —C(O)—NH-alkyl, and —C(O)-heterocycle; $R^5$, $R^6$ and $R^7$ are each independently selected from hydrogen, alkyl, —C(O)-alkyl, —C(O)-alkoxyalkyl, alkenyl, alkynyl, and heteroalkyl; $R^8$ is selected from hydrogen and alkyl; and $R^9$ is selected from hydrogen, alkyl, aryl, heteroaryl, arylalkyl, heterocycle, and heteroarylalkyl; and wherein said aryl, heteroaryl, cycloalkyl, and heterocycle, at each occurrence, unless otherwise stated, are independently substituted or unsubstituted.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together with the atoms to which they are attached form a ring; A is heteroaryl; D is hydrogen, halogen, nitro, alkyl, cyano, haloalkyl, cycloalkyl, aryl or heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O— alkoxyalkyl —C(O)—NH-alkyl, and —C(O)-heterocycle; $R^5$, $R^6$ and $R^7$ are each independently selected from hydrogen, alkyl, —C(O)-alkyl, —C(O)-alkoxyalkyl, alkenyl, alkynyl, and heteroalkyl; $R^8$ is selected from hydrogen and alkyl; and $R^9$ is selected from hydrogen, alkyl, aryl, heteroaryl, arylalkyl, heterocycle, and heteroarylalkyl; wherein said aryl, heteroaryl, cycloalkyl, and heterocycle, at each occurrence, unless otherwise stated, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkyl alkyl, heteroaryalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen and halogen; $R^4$ is selected from hydrogen, —C(O)-alkyl, —C(O)-alkenyl, —C(O)- alkoxyalkyl, —C(O)—O-alkyl, —C(O)—O-alkenyl, —C(O)—O— alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^4$ is selected from hydrogen, —C(O)-alkyl, —C(O)-alkenyl, —C(O)—O-alkyl, and —C(O)—O-alkenyl; $R^8$ is selected from hydrogen and alkyl; and $R^9$ is selected from alkyl, aryl, and heteroaryl.

In certain embodiments, $R^{1a}$ is $OR^4$; $R^{1d}$ is halogen or hydrogen; and $R^{1b}$, $R^{1c}$ and $R^{1e}$ are hydrogen.

In certain embodiments, $R^{1a}$ is $OR^4$; $R^{1d}$ is halogen; $R^{1b}$, $R^{1c}$ and $R^{1e}$ are hydrogen; and $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle.

In certain embodiments, $R^{1a}$ is $OR^4$; $R^{1d}$ is halogen; $R^{1b}$, $R^{1c}$ and $R^{1e}$ are hydrogen; and $R^4$ is selected from hydrogen, —C(O)-alkyl, —C(O)-alkenyl, —C(O)—O-alkyl, and —C(O)—O-alkenyl.

In certain embodiments, $R^{1a}$ is $OR^4$; $R^{1d}$ is halogen; $R^{1b}$, $R^{1c}$ and $R^{1e}$ are hydrogen; and $R^4$ is hydrogen.

In certain embodiments, A is a 5 or 6 membered heteroaryl. In certain embodiments, A is a 5 membered heteroaryl. In certain embodiments, A is a bicyclic heteroaryl.

In certain embodiments, D is a 6 membered aryl. In certain embodiments, D is hydrogen, halogen, nitro, alkyl, cyano or haloalkyl.

In certain embodiments, A is a bicyclic heteroaryl; and D is hydrogen, halogen, nitro, alkyl, cyano or haloalkyl.

In certain embodiments, $R^{1a}$ is $OR^4$; $R^{1d}$ is halogen; $R^{1b}$, $R^{1c}$ and $R^{1e}$ are hydrogen; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; A is a 5 or 6 membered heteroaryl; and D is a 6 membered aryl.

In certain embodiments, $R^{1a}$ is $OR^4$; $R^{1d}$ is halogen; $R^{1b}$, $R^{1c}$ and $R^{1e}$ are hydrogen; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; A is a bicyclic heteroaryl; and D is hydrogen, halogen, nitro, alkyl, cyano or haloalkyl.

Representative compounds of formula (I) include, but are not limited to:
4-chloro-2-(5-nitro-1H-benzo[d]imidazol-2-yl)phenol;
4-fluoro-2-(5-nitro-1H-benzo[d]imidazol-2-yl)phenol; and
4-chloro-2-(5-(4-nitrophenyl)-4H-1,2,4-triazol-3-yl)phenol;
or a pharmaceutically acceptable salt thereof.

In another aspect, disclosed is a compound of formula (II):

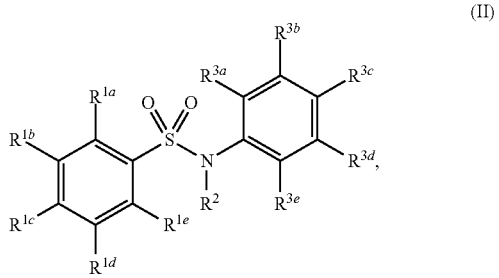

(II)

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together with the atoms to which they are attached form a ring; $R^2$ is selected from hydrogen, alkyl, —C(O)-alkyl, and —C(O)-alkenyl, or $R^2$ and $R^{1e}$ together with the atoms to which they are attached form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, $SO_2$—$R^9$ and $NR^8$—$SO_2$—$R^9$; $R^4$ is selected from hydrogen, alkyl, —C(O)-alkyl, —C(O)-alkenyl, C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, —C(O)—O-alkoxyalkyl, —C(O)—NH-alkyl, and —C(O)-heterocycle; $R^5$, $R^6$ and $R^7$ are each independently selected from hydrogen, alkyl, —C(O)-alkyl, —C(O)-alkenyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; R is selected from hydrogen and alkyl; and $R^9$ is selected from hydrogen, alkyl, aryl, heteroaryl, arylalkyl, heterocycle and heteroarylalkyl; and wherein said aryl, heteroaryl, and heterocycle, at each occurrence, unless otherwise stated, are independently substituted or unsubstituted.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together with the atoms to which they are attached form a ring; $R^2$ is selected from hydrogen, alkyl, —C(O)-alkyl, and —C(O)-alkenyl, or $R^2$ and $R^{1e}$ together with the atoms to which they are attached form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, $SO_2$—$R^9$ and $NR^8$—$SO_2$—$R^9$; $R^4$ is selected from hydrogen, alkyl, —C(O)-alkyl, —C(O)-alkenyl, C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, —C(O)—O-alkoxyalkyl, —C(O)—NH-alkyl, and —C(O)-heterocycle; $R^5$, $R^6$ and $R^7$ are each independently selected from hydrogen, alkyl, —C(O)-alkyl, —C(O)-alkenyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl; wherein said aryl, heteroaryl, and heterocycle, at each occurrence, unless otherwise stated, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylami no, sulfinylamino, sulfonyl, alkylsulfonyl, arylsulfonyl, aminosulfonyl, sulfinyl, —COOH, ketone, amide, carbamate, and acyl.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen and halogen; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^4$ is selected from hydrogen, —C(O)-alkyl, —C(O)-alkenyl, —C(O)—O-alkyl, and —C(O)—O-alkenyl; $R^8$ is selected from hydrogen and alkyl; and $R^9$ is selected from alkyl, aryl, and heteroaryl.

In certain embodiments, $R^{1a}$ is $OR^4$; $R^{1d}$ is halogen or hydrogen; and $R^{1b}$, $R^{1c}$ and $R^{1e}$ are hydrogen.

In certain embodiments, $R^{1a}$ is $OR^4$; $R^{1d}$ is halogen; $R^{1b}$, $R^{1c}$ and $R^{1e}$ are hydrogen; and $R^4$ is selected from —C(O)-alkyl, —C(O)-alkenyl, —C(O)—O-alkyl, and —C(O)—O-alkenyl.

In certain embodiments, $R^{1a}$ is $OR^4$; $R^{1d}$ is halogen; $R^{1b}$, $R^{1c}$ and $R^{1e}$ are hydrogen; and $R^4$ is hydrogen.

In certain embodiments, $R^2$ is selected from hydrogen and alkyl.

In certain embodiments, $R^2$ is selected from —C(O)-alkyl, —C(O)-alkenyl, —C(O)—O-alkenyl and —C(O)—O-alkyl.

In certain embodiments, $R^2$ and $R^{1e}$ together form a 5 to 8-membered ring. In certain embodiments, $R^2$ and $R^{1e}$ together form a 5-membered ring. In certain embodiments, $R^2$ and $R^{1e}$ together form a 6-membered ring. In certain embodiments, $R^2$ and $R^{1e}$ together form a 7-membered ring. In certain embodiments, $R^2$ and $R^{1e}$ together form an 8-membered ring.

In certain embodiments, $R^{3a}$, $R^{3b}$, $R^{3c}$, $R^{3d}$ and $R^{3e}$ are independently selected from hydrogen, halogen, nitro, $SO_2$—$R^9$ and haloalkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^2$ is selected from hydrogen and alkyl; $R^{3a}$, $R^{3b}$, $R^{3c}$, $R^{3d}$ and $R^{3e}$ are independently selected from hydrogen, halogen, nitro, $SO_2$—$R^9$ and haloalkyl; $R^4$ is selected from hydrogen, alkyl, and —C(O)-alkyl; $R^5$ is selected from hydrogen and alkyl and $R^9$ is selected from alkyl, aryl, and heteroaryl.

In certain embodiments, one of $R^{1a}$, $R^{1b}$, $R^{1c}$, $R^{1d}$ and $R^{1e}$ is $OR^4$ or $NR^8$—$SO_2$—$R^9$, and; $R^2$ is selected from hydrogen, —C(O)-alkyl, —C(O)-alkenyl, —C(O)—O-alkenyl and —C(O)—O-alkyl; $R^{3a}$, $R^{3b}$, $R^{3c}$, $R^{3d}$ and $R^{3e}$ are independently selected from hydrogen, halogen, nitro, $SO_2$—$R^9$ and haloalkyl; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^2$ is selected from hydrogen, —C(O)-alkyl, —C(O)-alkenyl, —C(O)—O-alkenyl and —C(O)—O-alkyl; $R^{3a}$, $R^{3b}$, $R^{3c}$, $R^{3d}$ and $R^{3e}$ are independently selected from hydrogen, halogen, nitro, $SO_2$—$R^9$ and haloalkyl; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

Representative compounds of formula (II) include, but are not limited to:

5-chloro-N-(2-chloro-4-(trifluoromethyl)phenyl)-2-hydroxybenzenesulfonamide;

or a pharmaceutically acceptable salt thereof.

In another aspect, disclosed is a compound of formula (III),

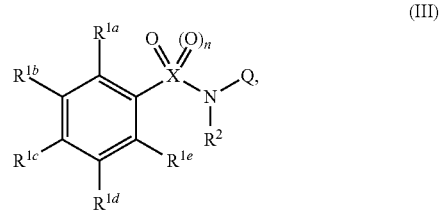

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together with the atoms to which they are attached form a ring; X is C or S; n is 0 or 1; $R^2$ is selected from hydrogen, alkyl, —C(O)-alkyl, and —C(O)-alkenyl, or $R^2$ and $R^{1e}$ together with the atoms to which they are attached form a ring; Q is heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl —C(O)—NH-alkyl, and —C(O)-heterocycle; $R^5$, $R^6$ and $R^7$ are each independently selected from hydrogen, alkyl, —C(O)-alkyl, —C(O)-alkoxyalkyl, alkenyl, alkynyl, and heteroalkyl; $R^8$ is selected from hydrogen and alkyl; and $R^9$ is selected from hydrogen, alkyl, aryl, heteroaryl, arylalkyl, heterocycle, and heteroarylalkyl; and wherein said aryl, heteroaryl, and heterocycle, at each occurrence, unless otherwise stated, are independently substituted or unsubstituted.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and NR$^8$—SO$_2$—R$^9$; or R$^{1b}$ and R$^{1c}$, R$^{1c}$ and R$^{1d}$, or R$^{1d}$ and R$^{1e}$ together with the atoms to which they are attached form a ring; X is C or S; n is 0 or 1; R$^2$ is selected from hydrogen, alkyl, —C(O)-alkyl, and —C(O)-alkenyl, or R$^2$ and R$^{1e}$ together with the atoms to which they are attached form a ring; Q is heteroaryl, with 0-5 substituents independently selected from hydrogen, halogen, nitro, alkyl, cyano, haloalkyl, alkoxyalkyl, heteroalkyl, alkenyl, alkynyl, heterocycle, carboxyl, heterocyclealkyl, OR$^4$, SR$^5$, NR$^6$R$^7$, and NR$^8$—SO$_2$—R$^9$; R$^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl —C(O)—NH-alkyl, and —C(O)-heterocycle; R$^5$, R$^6$ and R$^7$ are each independently selected from hydrogen, alkyl, —C(O)-alkyl, —C(O)-alkoxyalkyl, alkenyl, alkynyl, and heteroalkyl; R$^8$ is selected from hydrogen and alkyl; and R$^9$ is selected from hydrogen, alkyl, aryl, heteroaryl, arylalkyl, heterocycle, and heteroarylalkyl; and wherein said aryl, heteroaryl, and heterocycle, at each occurrence, unless otherwise stated, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, R$^{1a}$ is OR$^4$ or NR$^8$—SO$_2$—R$^9$; R$^{1b}$, R$^{1c}$ and R$^{1e}$ are hydrogen; R$^{1d}$ is halogen; R$^2$ is hydrogen, alkyl, —C(O)-alkyl or —C(O)-alkenyl; R$^4$ is selected from hydrogen, —C(O)-alkyl, —C(O)-alkenyl, —C(O)—O-alkenyl or —C(O)—O-alkyl; R$^8$ is selected from hydrogen and alkyl; and R$^9$ is selected from alkyl, aryl, and heteroaryl.

In certain embodiments, R$^{1a}$ is OR$^4$; R$^{1b}$, R$^{1c}$ and R$^{1e}$ are hydrogen; R$^{1d}$ is halogen; R$^2$ is hydrogen, alkyl, —C(O)-alkyl or —C(O)-alkenyl; and R$^4$ is selected from hydrogen, —C(O)-alkyl, —C(O)-alkenyl, —C(O)—O-alkenyl or —C(O)—O-alkyl.

In certain embodiments, R$^{1a}$ is OR$^4$; R$^{1b}$, R$^{1c}$ and R$^{1e}$ are hydrogen; R$^{1d}$ is halogen; R$^2$ is hydrogen or alkyl; and R$^4$ is selected from hydrogen, —C(O)-alkyl, —C(O)-alkenyl, —C(O)—O-alkenyl or —C(O)—O-alkyl.

In certain embodiments, R$^{1a}$ is OR$^4$; R$^{1d}$ is halogen; R$^{1b}$, R$^{1c}$ and R$^{1e}$ are hydrogen; and R$^4$ is hydrogen.

In certain embodiments, Q is a 5 or 6 membered heteroaryl. In certain embodiments, Q is a 5 membered heteroaryl. In certain embodiments, Q is a 6 membered heteroaryl.

In certain embodiments, X is C and n is 0. In certain embodiments, X is S and n is 1. In certain embodiments, X is S and n is 0.

In certain embodiments, R$^{1a}$ is OR$^4$; R$^{1b}$, R$^{1c}$ and R$^{1e}$ are hydrogen; R$^{1d}$ is halogen; R$^2$ is hydrogen or alkyl; and R$^4$ is selected from hydrogen, —C(O)-alkyl, —C(O)-alkenyl, —C(O)—O-alkenyl or —C(O)—O-alkyl; X is C; n is 0; and Q is a 5 membered heteroaryl.

Representative compounds of formula (III) include, but are not limited to:
2-hydroxy-N-(5-nitrothiazol-2-yl)benzamide; and
2-((5-nitrothiazol-2-yl)carbamoyl)phenyl acetate,
or a pharmaceutically acceptable salt thereof.

In another aspect, disclosed are the following compounds:
4-chloro-2-((2-chloro-4-nitrophenyl)carbamoyl)phenyl octanoate;
6-chloro-2-(trifluoromethyl)-N-(4-(trifluoromethyl)phenyl)-1H-benzo[d]imidazole-4-carboxamide;
5-chloro-N-(2-chloro-4-(trifluoromethyl)phenyl)-2-hydroxybenzamide;
5-chloro-N-(3,5-dichlorophenyl)-2-hydroxybenzamide;
5-bromo-2-((4-methylphenyl)sulfonamido)-N-(4-(trifluoromethyl)phenyl)benzamide; and
(2-butylbenzofuran-3-yl)(4-(2-(diethylamino)ethoxy)-3,5-diiodophenyl)methanone, or a pharmaceutically acceptable salt thereof.

In another aspect, disclosed are the following compounds:
4-chloro-2-((2-chloro-4-nitrophenyl)carbamoyl)phenyl octanoate;
6-chloro-2-(trifluoromethyl)-N-(4-(trifluoromethyl)phenyl)-1H-benzo[d]imidazole-4-carboxamide;
5-chloro-N-(2-chloro-4-(trifluoromethyl)phenyl)-2-hydroxybenzamide;
5-chloro-N-(3,5-dichlorophenyl)-2-hydroxybenzamide;
5-bromo-2-((4-methylphenyl)sulfonamido)-N-(4-(trifluoromethyl)phenyl)benzamide;
5-chloro-N-(2-chloro-4-nitrophenyl)-2-hydroxybenzamide;
6-((3R,4S,5S,7R)-7-((2S,3S,5S)-5-ethyl-5-((2R,5R,6S)-5-ethyl-5-hydroxy-6-methyltetrahydro-2H-pyran-2-yl)-3-methyltetrahydrofuran-2-yl)-4-hydroxy-3,5-dimethyl-6-oxononyl)-2-hydroxy-3-methylbenzoic acid;
(2-butylbenzofuran-3-yl)(4-(2-(diethylamino)ethoxy)-3,5-diiodophenyl)methanone;
3,3-diphenyl-N-(1-phenylethyl)propan-1-amine;
N4-(6-chloro-2-methoxyacridin-9-yl)-N1,N1-diethylpentane-1,4-diamine;
(1$^1$S,3$^1$S)-1$^6$,3$^6$,3$^7$,5$^4$-tetramethoxy-1$^2$,3$^2$-dimethyl-1$^1$,1$^2$, 1$^3$,1$^4$,3$^1$,3$^2$,3$^3$,3$^4$-octahydro-2,6-dioxa-1(7,1),3(8,1)-diisoquinolina-5(1,3),7(1,4)-dibenzenacyclooctaphane; and
2-[(E)-2-(2,5-Dimethyl-1-phenylpyrrol-3-yl)ethenyl]-N,N,1-trimethylquinolin-1-ium-6-amine;

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present invention also includes an isotopically-labeled compound, which is identical to those recited in the present disclosure, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of the present disclosure are $^{11}$C, $^{13}$N, $^{15}$O, and $^{18}$F. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. General Synthesis

1. Compounds of Formula (I)

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^{1a}$, $R^{1b}$, $R^{1c}$, $R^{1d}$, $R^{1e}$ and D have the meanings as set forth in the Summary of the Invention section, and A is a bicyclic heteroaryl, can be synthesized as shown in Scheme 1.

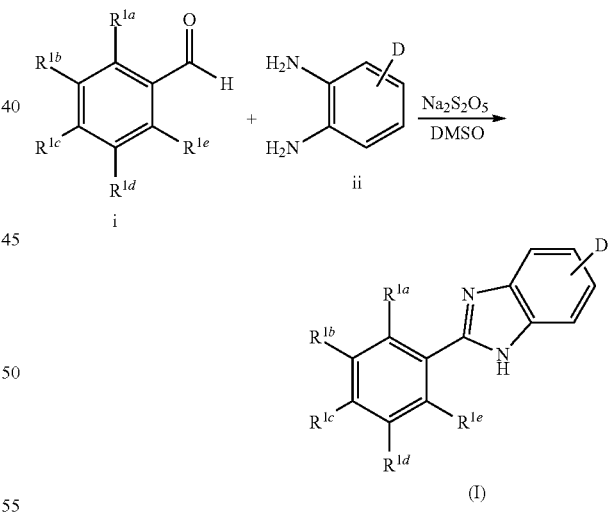

As shown in Scheme 1, treatment of substituted benzaldehyde i, wherein $R^{1a}$, $R^{1b}$, $R^{1c}$, $R^{1d}$ and $R^{1e}$ are as defined in the Summary of the Invention, with ii, wherein D is defined in the Summary of the Invention, in the presence of sodium metabisulfite can provide the compound of formula (I), wherein A is a bicyclic heteroaryl.

Compounds of formula (I), wherein the groups $R^{1a}$, $R^{1b}$, $R^{1c}$, $R^{1d}$, $R^{1e}$ and D have the meanings as set forth in the Summary of the Invention, and A is a 5-membered heteroaryl, can be synthesized as shown in Scheme 2.

Scheme 2. Synthesis of the compound of formula (I)

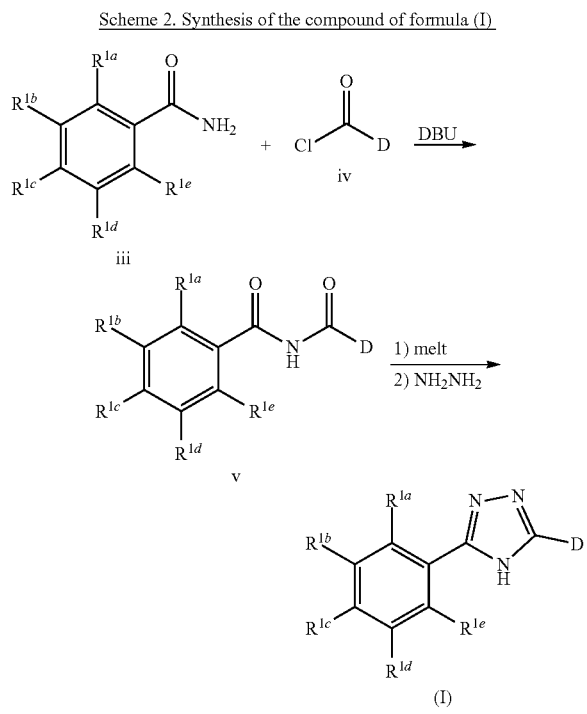

As shown in Scheme 2, intermediate v, wherein $R^{1a}$, $R^{1b}$, $R^{1c}$, $R^{1d}$ and $R^{1e}$ are as defined in the Summary of the Invention, can be prepared by the coupling of benzamide iii with acid chloride iv, wherein D is as defined in the Summary of the Invention. Treatment of v with hydrazine can provide the compound of formula (I).

2. Compounds of Formula (II)

Compounds of formula (II), wherein the groups $R^{1a}$, $R^{1b}$, $R^{1c}$, $R^{1d}$, $R^{1e}$, $R^2$, $R^{3a}$, $R^{3b}$, $R^{3c}$, $R^{3d}$ and $R^{3e}$ have the meanings as set forth in the Summary of the Invention section unless otherwise noted, can be synthesized as shown in Scheme 3.

Scheme 3. Synthesis of the compound of formula (II)

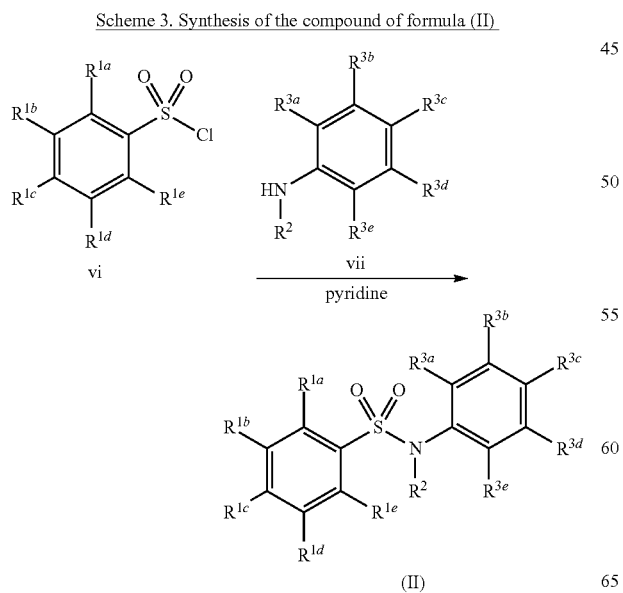

As shown in Scheme 3, intermediate vi, wherein $R^{1a}$, $R^{1b}$, $R^{1c}$, $R^{1d}$ and $R^{1e}$ are as defined in the Summary of the Invention, can be coupled with aniline vii, wherein $R^{3a}$, $R^{3b}$, $R^{3c}$, $R^{3d}$ and $R^{3e}$ are as defined in the Summary of the Invention, in the presence of pyridine to provide the compound of formula (II).

3. Compounds of Formula (III)

Compounds of formula (III), wherein the groups $R^{1a}$, $R^{1b}$, $R^{1c}$, $R^{1d}$, $R^{1e}$, $R^2$, and Q have the meanings as set forth in the Summary of the Invention section and X is S and is 1, can be synthesized as shown in Scheme 4.

Scheme 4. Synthesis of the compound of formula (III)

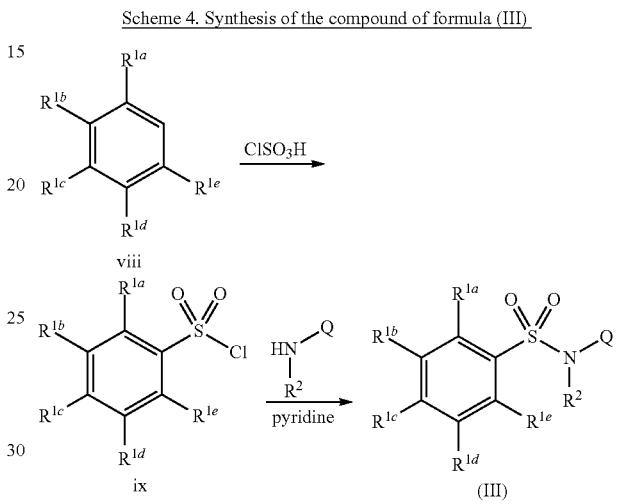

As shown in Scheme 4, intermediate ix, wherein $R^{1a}$, $R^{1b}$, $R^{1c}$, $R^{1d}$ and $R^{1e}$ are as defined in the Summary of the Invention, can be prepared from the substituted benzene, viii, and chlorosulfonic acid. Treatment of ix with an amine, wherein $R^2$ and Q are as defined in the Summary of the Invention, can provide the compound of formula (III).

Compounds of formula (III), wherein the groups $R^{1a}$, $R^{1b}$, $R^{1c}$, $R^{1d}$, $R^{1e}$, $R^2$, and Q have the meanings as set forth in the Summary of the Invention section and X is C and n is 0, can be synthesized as shown in Scheme 5.

Scheme 5. Synthesis of the compound of formula (III)

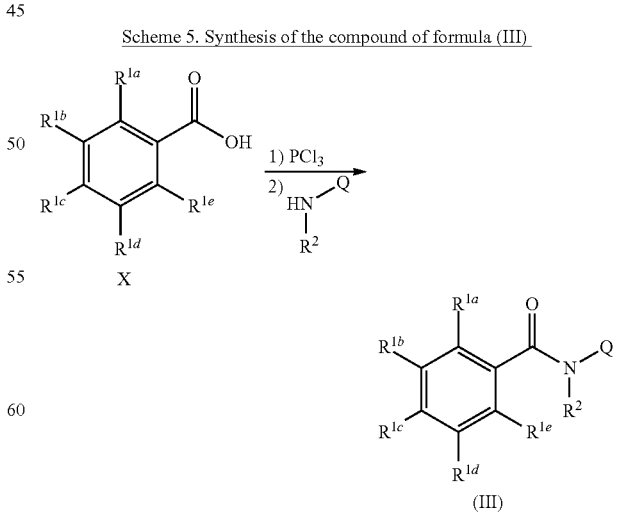

Benzoic acid x, wherein $R^{1a}$, $R^{1b}$, $R^{1c}$, $R^{1d}$ and $R^{1e}$ are as defined in the Summary of the Invention, can be transformed to the acid chloride by treatment with $PCl_3$. The acid chloride intermediate can be treated with an amine, wherein $R^2$ and Q are as defined in the Summary of the Invention, to provide the compound of formula (III).

Employing analogous synthetic methods and the syntheses provided in the Examples, the remaining compounds of the disclosure may be obtained.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety.

Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

4. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound, and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The compounds and processes of the invention will be better understood by reference to the following examples, which are intended as an illustration of and not a limitation upon the scope of the invention.

5. EXAMPLES

Example 1. 4-Chloro-2-(5-(4-nitrophenyl)-4H-1,2,4-triazol-3-yl)phenol (1)

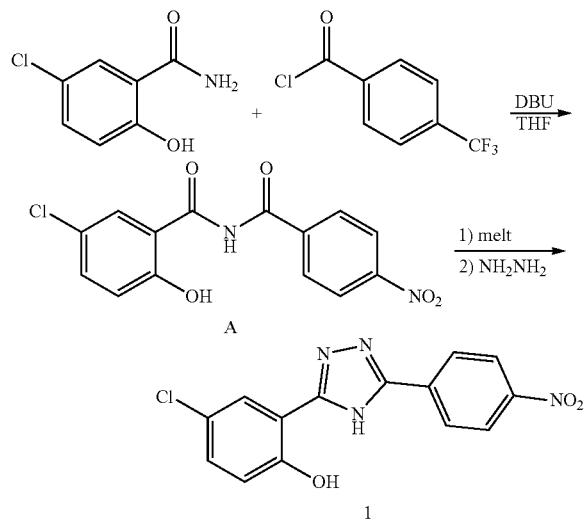

5-Chloro-2-hydroxy-N-(4-nitrobenzoyl)benzamide (A)

To a dry round-bottom flask equipped with a magnetic stir bar under an Argon atmosphere was added 5-chloro-2-hydroxybenzamide (0.526 g; 3.07 mmol), 8 mL dry acetonitrile, and 1 mL 1,8-diazabicyclo[5.4.0]undec-7-ene (DBU). To this solution was added 4-nitrobenzoyl chloride (0.57 g; 3.07 mmol). The reaction was followed by TLC until complete. To the reaction mixture was added 20 mL of water and 1 mL of conc. HCl. The resultant white heterogeneous suspension was stirred for 5 min and filtered on paper under vacuum. The precipitate was rinsed with water before suspending the solids in water, filtering, and drying the solids in the filter funnel under vacuum to give a white solid (0.750 g). The solids were triturated with methanol/acetonitrile (1:1), filtered and dried in air in the filter funnel under vacuum to give the title compound as a cream colored solid. $^1$H NMR (400 MHz, DMSO-$d_6$) δ 8.34 (d, J=9 Hz, 2H), 8.11 (d, J=9 Hz, 2H), 7.67 (d, J=3 Hz, 1H), 7.36 (dd, J=9, 2.3 Hz, 1H), 6.87 (d, J=8.8 Hz, 1H). MS (ESI−) m/z=319, 321 (3:1) (M−1).

4-Chloro-2-(5-(4-nitrophenyl)-4H-1,2,4-triazol-3-yl)phenol (1)

To a dry vial equipped with a magnetic stir bar under an atmosphere of argon was added A (0.196 g; 0.61 mmol). The vial was placed in a sand bath at ca. 270° C. which caused the solids to melt. The resultant liquid was stirred for 5 minutes at 270° C. and then allowed to cool to room temperature. A portion of the resultant solid was transferred to a round bottom flask equipped with a reflux condenser. The solids were suspended in 10 mL of ethanol (95%) and treated with 2 equivalents of hydrazine hydrate. The resultant mixture was heated to reflux for 2 hours and then allowed to stand overnight at room temperature. Water and methylene chloride were added, and the aqueous layer was separated and extracted 2 times with methylene chloride. The pH of the aqueous layer was adjusted to 7 with dilute HCl and re-extracted with methylene chloride. The methylene chloride layers were combined, dried over sodium sulfate, filtered and concentrated to dryness. The solids were purified by reverse phase HPLC using an aqueous gradient of 5-100% methanol containing 0.2% formic acid. The desired material was isolated by lyophilization to give 0.01 g of the title compound as a light yellow solid. $^1$H NMR (500 MHz, DMSO-$d_6$) δ 8.34-8.42 (m, 4H), 8.06 (d, J=1.95 Hz, 1H), 7.42 (dd, J=8.8, 2.0, Hz, 1H), 7.08 (d, J=8.8 Hz, 1H). HRMS m/z=317.0436 (M+1).

Example 2. 4-Chloro-2-(5-nitro-1H-benzo[d]imidazol-2-yl)phenol (2)

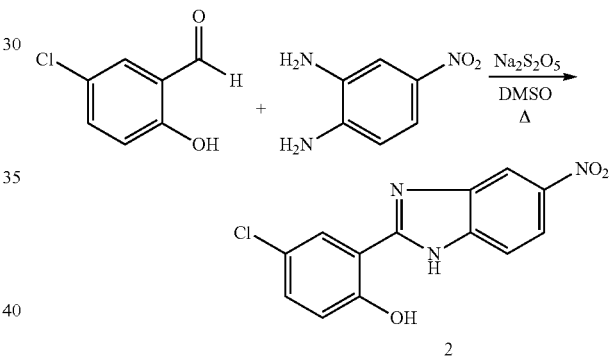

4-Chloro-2-(5-nitro-1H-benzo[d]imidazol-2-yl)phenol (2)

To a round-bottom flask equipped with a reflux condenser was added 5-chloro-2-hydroxybenzaldehyde (0.448 g; 2.86 mmol), DMSO (4 mL) and 4-nitrobenzene-1,2-diamine (0.431 g; 2.86 mmol). To the resulting deep red solution was added sodium metabisulfite (0.181 g; 0.95 mmol) and the resultant mixture was allowed to stir at 160° C. for 2 hr. The reaction mixture was subsequently cooled to rt and poured into 100 mL of water, and the resultant mixture stirred for 1 hr, filtered, rinsed with water, and dried in air under vacuum in the filter funnel to give 0.848 g of a brown solid. The desired material can be purified by RPHPLC or by silica gel chromatography. A portion of the solids (0.152 g) was purified by C18 reverse phase chromatography using a gradient of 5-98% MeOH/water containing 0.2% formic acid. The remaining solids were purified by adsorbing on 2.5 mL of silica gel and eluting silica gel on 20 mL of silica gel with a gradient of 0-3% EtOAc/CHCl$_3$. The desired fractions were combined and concentrated in vacuo to give 0.0435 g of the title compound as a yellow solid. $^1$H NMR (400 MHz, DMSO-$d_6$) δ 12.9 (br s, 1H) 8.54 (br. s, 1H), 8.18

(d, J=2.6 Hz, 1H), 8.12-8.16 (m, 1H), 7.81 (d, J=8.9 Hz, 1H), 7.40-7.47 (m, 1H), 7.09 (d, J=8.8 Hz, 1H). MS (ESI−) m/z=288, 290 (M−1).

The following compound was made employing analogous synthetic procedures:

| No. | Starting Material | Compound | MS (m/z) |
|---|---|---|---|
| 3 | 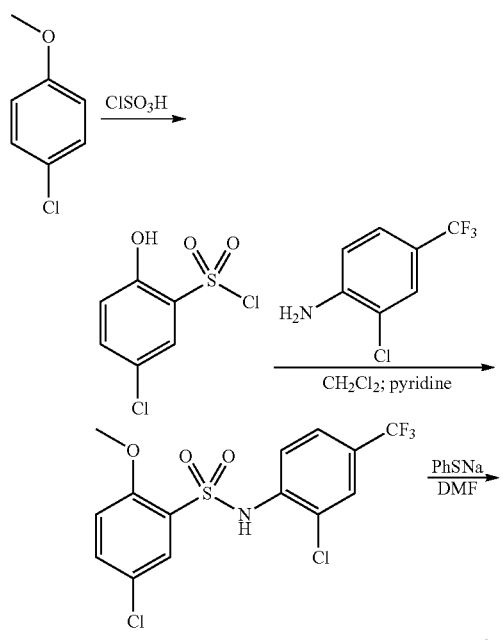 | | (ESI−) = 272 (M − 1) |

4-fluoro-2-(5-nitro-1H-benzo[d]imidazol-2-yl)phenol

Example 3. 5-Chloro-N-(2-chloro-4-(trifluoromethyl)phenyl)-2-hydroxybenzenesulfonamide (4)

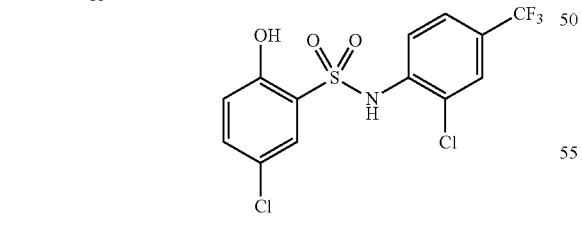

4

5-Chloro-N-(2-chloro-4-(trifluoromethyl)phenyl)-2-hydroxybenzenesulfonamide (4)

p-Chloroanisole was chlorosulfonylated using the method of Guo (Guo, et al. *Tetrahedron* 1997, 53, 4145) to produce 5-chloro-2-methoxybenzenesulfonyl chloride which was used without purification. To an ice-cold solution of 5-chloro-2-methoxybenzenesulfonyl chloride (0.398 g, 1.8 mmol), CH$_2$Cl$_2$ (5 mL) and pyridine (0.28 g, 3.6 mmol) was added 2-chloro-4-(trifluoromethyl)aniline (0.347 g, 0.18 mmol) over 1 min. After the reaction was complete by HPLC/MS, water was added and the reaction mixture was extracted with CH$_2$Cl$_2$. The CH$_2$Cl$_2$ layer was washed three times with dilute acid, one time with brine, dried over Na$_2$SO$_4$, and filtered through glass wool. The filtrate containing 5-chloro-N-(2-chloro-4-(trifluoromethyl)phenyl)-2-methoxybenzenesulfonamide was concentrated and used directly without further purification. To a dry round-bottom flask containing 5-chloro-N-(2-chloro-4-(trifluoromethyl)phenyl)-2-methoxybenzenesulfonamide in dry DMF (5 mL) was added a solution of freshly prepared 1M sodium benzenethiolate in DMF (3.6 mL). The resultant dark colored mixture was heated in an oil bath at 135-145° C. for 3.5 h, cooled to rt, poured into water (100 mL), and the aqueous mixture extracted 2 times with EtOAc. The EtOAc layers were combined, washed 5 times with water, 1 time with brine, dried with Na$_2$SO$_4$, decanted, and concentrated onto 5 mL of silica gel. The solids were eluted on a column of 100 mL of silica gel with a gradient of 10-30% EtOAc/Hexane. The material with rf=0.25 (25% EtOAc/Hexane) was combined and concentrated to give 0.22 g of the title compound as a light tan solid. H NMR (300 MHz, DMSO-d$_6$) δ 11.3 (br s, 1H), 9.9 (br s, 1H), 7.83 (s, 1H), 7.66-7.47 (m, 4H), 6.98 (d, J=8.8, 1H). m/z (ESI−)=384, 386 (M−1). FTIR (thin film) 3339 br, 1615 w, 1323 st, m/z (ESI−)=384, 386 (M−1).

Example 4. Anilide Synthesis

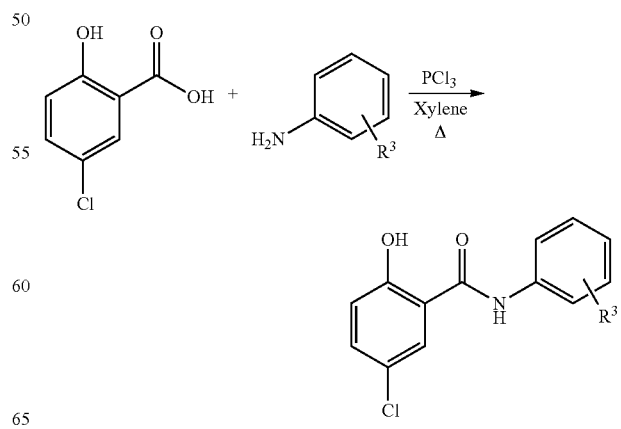

General Method:

To a 100 mL flask equipped with a reflux condenser was added 5-chloro-2-hydroxybenzoic acid (1 equiv.), the aniline derivative (1 equiv.), and dry xylenes (stored over 3 A molecular sieves, 40 mL per gram of 5-chloro-2-hydroxybenzoic acid) under an atmosphere of argon. The mixture was heated to reflux, and PCl₃ (0.4 equiv.) was added rapidly via syringe. The mixture was heated at reflux for 1 hour and cooled to room temperature. Water (40 mL per gram of 5-chloro-2-hydroxybenzoic acid) was added and the resultant heterogeneous mixture stirred rapidly for 1 hour. Saturated sodium bicarbonate was added to a final pH of 3-4, and the mixture stirred rapidly overnight. The solids were filtered and washed sequentially with water, toluene and hexane. Samples were analyzed by NMR, HPLC/mass spectrometry and TLC. Purification by crystallization or column chromatography on silica gel was performed when purity was less than 95% by LC. HPLC/MS was accomplished using an Agilent spectrometer—6310 Ion trap. Mass ions (m/z) detected in positive ionization mode are M+; in negative ionization mode, mass ions (m/z) are M−.

The following compounds were made employing analogous synthetic procedures:

| No. | Aniline Starting Material | Compound | MS (m/z) |
|---|---|---|---|
| 5 | Cl, CF₃, H₂N (2-chloro-4-(trifluoromethyl)aniline) | 5-chloro-N-(2-chloro-4-(trifluoromethyl)phenyl)-2-hydroxybenzamide | (ESI−) = 348, 350 (M − 1) |
| 6 | Cl, Cl, H₂N (3,5-dichloroaniline) | 5-chloro-N-(3,5-dichlorophenyl)-2-hydroxybenzamide | (ESI−) = 314, 316 (M − 1) |

Example 5. 4-Chloro-2-((2-chloro-4-nitrophenyl)carbamoyl)phenyl octanoate (7)

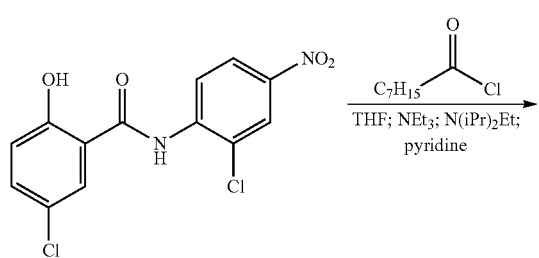

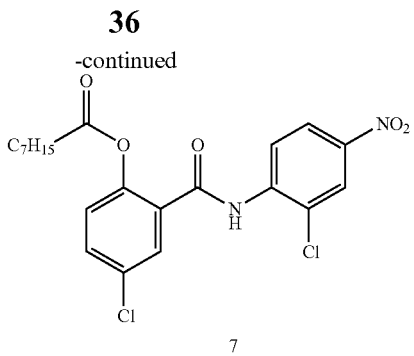

4-Chloro-2-((2-chloro-4-nitrophenyl)carbamoyl) phenyl Octanoate (7)

To a dry 500 mL round-bottomed 3-neck flask equipped with thermometer and addition funnel under an argon atmosphere, was added CH₂Cl₂ (80 mL) and oxalyl chloride (7 mL, 0.083 mol). To the addition funnel was added CH₂Cl₂ (10 mL), DMF (0.5 mL), and octanoic acid (11 mL, 0.069 mol) and this solution added drop-wise over 8 min (rapid gas evolution). After addition was complete the reaction mixture was stirred at rt for 2 hours. Dioxane (20 mL) was added and the flask was fitted with a distillation head. The reaction mixture was concentrated under house vacuum with heating (45-50° C.) to a volume between 10-15 mL. This concentrated mixture was then cooled to room temperature and dry THF (100 mL) was added. In a separate flask was added niclosamide (22.7 g, 0.069 mol), dry THF (200 mL) and to this suspension was added triethylamine (16 mL) and DIEA (10 mL). A majority of the solids dissolved and this mixture was added to the addition funnel, along with 10 mL of dry pyridine. Upon addition of the pyridine a precipitate formed that was suspended in an additional 150 mL of dry THF. This mixture was added to the solution of octanoyl chloride over a total of 15 min. As the niclosamide suspension was added to the acid chloride, the internal temperature began to increase to 28° C. at which point an ice-bath was provided to maintain the temperature between 15-25° C. during the addition. The resultant mixture was stirred over night at room temperature and monitored by HPLC and TLC (30% EtOAC/hexane). The reaction mixture was poured into water and concentrated. The concentrate was diluted with $CH_2Cl_2$ and 1N HCl and the mixture filtered. The precipitate was washed with $CH_2Cl_2$ and the $CH_2Cl_2$ wash combined with the filtrate. The $CH_2Cl_2$ layers were combined and were washed three times with 1N HCl, one time with brine, dried over $Na_2SO_4$, filtered and concentrated onto 25 mL of silica gel. The solids were eluted from a column of 200 mL of silica gel using a gradient of 7.8:2:0.2 to 7.5:2.5:0.2 hexane/chloroform/EtOAc. The fractions containing the desired compound were combined, heptane was added and the solution concentrated until a large volume of white precipitate was observed. The suspension was allowed to stand overnight, and the precipitate filtered, washed with hexane and dried under vacuum to yield 14.19 g (32.5% over two steps) of the title compound as a white solid. $^1$H NMR (400 MHz, DMSO-$d_6$) δ 10.44 (s, 1H), 8.40 (d, J=2.59 Hz, 1H), 8.27 (dd, J=9.03, 2.59 Hz, 1H), 8.13 (d, J=9.08 Hz, 1H), 7.82 (d, J=2.64 Hz, 1H), 7.69 (dd, J=8.69, 2.64 Hz, 1H), 7.34 (d, J=8.69 Hz, 1H), 2.54 (t, J=7.32 Hz, 2H), 1.48-1.59 (m, 2H), 1.05-1.28 (m, 8H), 0.79 (t, J=7.03 Hz, 3H). $^{13}$C (125 MHz, DMSO-$d_6$) 171.76, 163.67, 147.24, 144.75, 141.22, 132.35, 130.61, 130.42, 129.57, 127.24, 126.02, 125.89, 125.47, 123.53, 33.89, 31.54, 28.87, 28.74, 24.59, 22.50, 14.33. FTIR (thin film) 3362 st, 2950 st, 2935 st, 2855 st, 1770 st, 1685 st, m/z (ESI+)=453, 455 (M+1).

Example 6. 5-Bromo-2-((4-methylphenyl)sulfonamido)-N-(4-(trifluoromethyl)phenyl)benzamide (8)

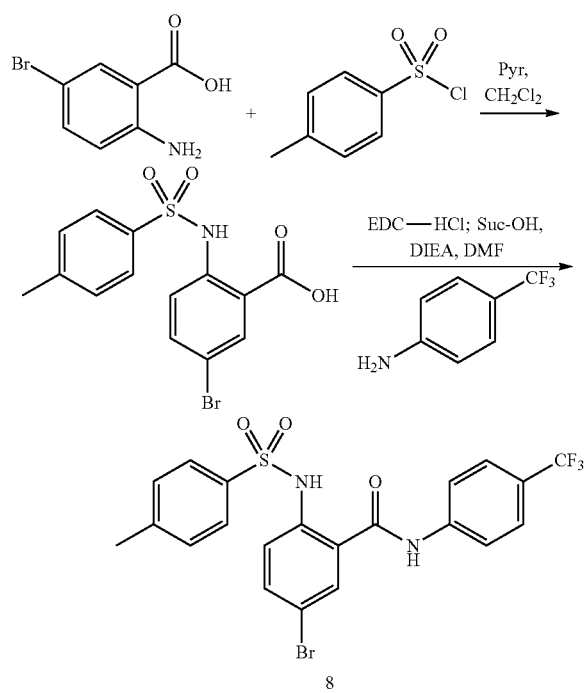

5-bromo-2-((4-methylphenyl)sulfonamido)-N-(4-(trifluoromethyl)phenyl)benzamide (8)

To a dry, round-bottom flask under an atmosphere of argon, was added p-tosyl chloride (1.88 g; 9.9 mmol), methylene chloride (20 mL), and dry pyridine (2.17 mL; 27 mmol). The reaction mixture was cooled in an ice-bath and 2-amino-5-bromobenzoic acid (1.94 g; 9 mmol) was added as a solid over 30 secs. To the resultant heterogeneous suspension was added dry pyridine (2.17 mL; 27 mmol) to produce a light brown solution. The reaction mixture was allowed to warm to room temperature while stirring overnight. The reaction mixture was then washed 4 times with 1 N HCl, and the organic layers were dried over $Na_2SO_4$, filtered, and concentrated to a yellow foam, which was used without further purification. A portion of this material (0.27 g) was transferred to a dry round-bottom flask and dissolved in dry DMF. To this solution was added N-(3-dimethylaminopropyl)-N'-ethylcarbodiimide hydrochloride (0.153 g; 0.81 mmole), N-hydroxysuccinimide (0.092 g; 0.81 mmole), N,N-diisopropylethylamine (0.28 mL; 1.6 mmol) and 4-(trifluoromethyl)aniline (0.12 g; 0.745 mmol) 4-(trifluoromethyl)aniline. The reaction was monitored by TLC (eluent: 10% MeOH/$CH_2Cl_2$). Upon completion, the reaction mixture was poured into 75 mL of water and extracted two times with ethyl acetate. The ethyl acetate layers were combined and washed 5 times with dilute phosphate buffer (pH=5-6), one time with dilute aq. HCl, one time with brine solution, dried over sodium sulfate and filtered. The filtrate was concentrated onto a plug of silica gel and the silica gel added to a column of 25 mL of silica gel packed in 5% methanol/methylene chloride. The column was eluted with a gradient of 5-10% methanol/methylene chloride. Mixed fractions containing the desired compound were combined and purified by C-18 reverse phase HPLC (aqueous gradient of 5-100% MeOH containing 0.2% formic acid) to give 26 mg of the title compound as a white solid. $^1$H NMR (400 MHz, DMSO-$d_6$) δ 10.62 (br s, 1H), 10.25 (br. s, 1H), 7.89 (d, J=1 Hz, 1H), 7.87 (d, J=8.5 Hz, 2H), 7.75 (d, J=8.5 Hz, 2H), 7.7 (d, J=7.9 Hz, 1H), 7.61 (d, J=8.2 Hz, 2H), 7.31 (d, J=8.7 Hz, 1H), 7.26 (d, J=8.2 Hz, 2H), 2.27 (s, 3H). MS (ESI−) m/z=511, 513 (M−1).

Example 7. 6-Chloro-2-(trifluoromethyl)-N-(4-(trifluoromethyl)phenyl)-1H-benzo[d]imidazole-4-carboxamide (9)

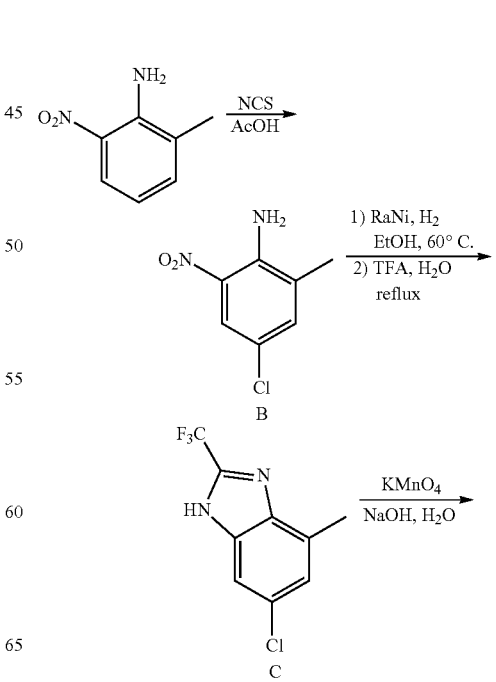

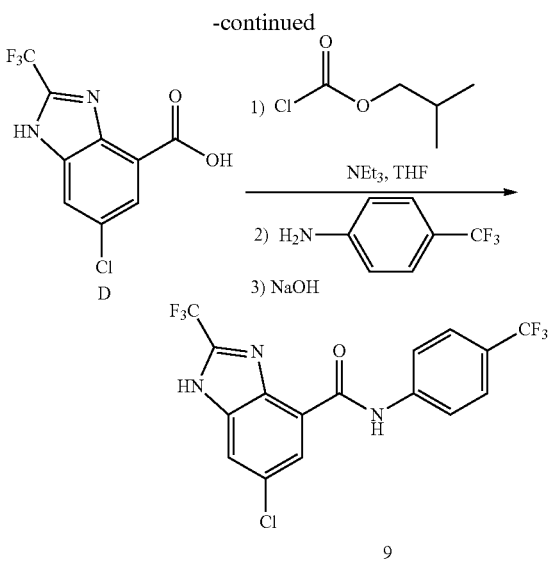

4-Chloro-2-methyl-6-nitroaniline (B)

To a 2-necked round-bottom flask equipped with an addition funnel, a thermometer and a magnetic stir bar under an atmosphere of argon, was added 2-methyl-6-nitroaniline (12.97 g; 85.23 mmol) and glacial acetic acid (35 mL). The suspension was placed in a pre-heated oil bath at 50° C. to produce a red solution. To the addition funnel was added a suspension of 11.95 g N-chlorosuccinimide (NCS) in about 45 mL of acetic acid. The NCS suspension was added dropwise over about 15 minutes while maintaining the temperature at about 55° C. After the addition was complete, the addition funnel was rinsed with acetic acid (ca. 5 mL) and added to the reaction mixture. A brown homogeneous solution resulted during the course of the reaction. The progress of the reaction was followed by TLC (eluent: methylene chloride). Upon completion of the reaction, the reaction mixture was cooled to room temperature and poured into 100 mL of water and then cooled in an ice bath. The solids were filtered on paper under vacuum, and rinsed with 130 mL of water. The solids were dried in the filter funnel under vacuum to yield 13.3 g of the title compound as an orange-red solid. $^1$H NMR (400 MHz, DMSO-$d_6$) δ 7.82 (d, J=2.2 Hz, 1H), 7.38 (br. s, 1H), 7.23 (br. s., 2H), 2.17 (s, 3H). MS (ESI+) m/z=187 (M+1). This material was used in the subsequent reactions without further purification.

6-Chloro-4-methyl-2-(trifluoromethyl)-1H-benzo[d]imidazole (C)

To a round-bottom flask equipped with a Claisen adapter and a magnetic stir bar under an atmosphere of argon was added 2.24 g (11.95 mmol) of B and 95% ethanol (56 mL). To this mixture was added an aqueous (pH 7-8) suspension of RaNi (~2 g). The reaction flask was evacuated and charged 3 times with hydrogen, and then placed in an oil bath pre-heated to 60-70° C. After 4 hr, the reaction was complete by TLC (3% methanol/methylene chloride). The flask was evacuated and charged 3-4 times with Argon, and celite was added. The mixture was filtered through celite, rinsed sequentially with ethanol and then water, and the filtrate concentrated in vacuo to a brown oil. The oil was suspended in water (40 mL) and 2.7 mL of trifluoroacetic acid was added, and the resultant mixture heated to reflux for 2.5 hr. The reaction mixture was then cooled to room temperature. Sodium bicarbonate was added carefully to adjust the pH to 7-8, and the aqueous reaction mixture extracted 2 times with ethyl acetate. The ethyl acetate layers were combined, washed with brine, dried over sodium sulfate, filtered, and concentrated in vacuo to give the title compound as a solid. MS (ESI+) m/z=235, 233 (M+1). This material was used in subsequent reactions without further purification.

6-Chloro-2-(trifluoromethyl)-1H-benzo[d]imidazole-4-carboxylic Acid (D)

To a round-bottom flask equipped with a magnetic stir bar, and a thermometer and reflux condenser was added C (2.11 g; 9 mmol) and 0.5 M NaOH (126 mL). The reaction mixture was heated to reflux and KMnO$_4$ (7.56 g; 44.97 mmol) was added in 5 portions over 4 hours, and the resulting mixture was heated at reflux for 3 additional hours. The reaction mixture was removed from the oil bath and allowed to cool to 50° C. Celite and sodium metabisulfite was added to the reaction flask, and the mixture filtered hot through celite. The filtrate was cooled in an ice bath, and HCl added to adjust the pH to 3. The resultant aqueous mixture was extracted 3 times with ethyl acetate, and the ethyl acetate layers were combined, dried over sodium sulfate, filtered, and concentrated onto a plug of silica gel. The silica gel plug was loaded onto a column of silica gel and the product was eluted with 10-80% methanol/methylene chloride. The desired fractions were combined, heptane added, and concentrated in vacuo to give 0.9 g of the title compound as a white-tan solid. $^1$H NMR (400 MHz, DMSO-$d_6$) δ 8.18 (s, 1H), 7.89 (s, 1H). MS (ESI−) m/z=263, 265 (M−1).

6-Chloro-2-(trifluoromethyl)-N-(4-(trifluoromethyl)phenyl)-1H-benzo[d]imidazole-4-carboxamide (9)

To a dry round-bottom flask was added D (0.105 g; 0.398 mmol), dry THF (3 mL), and triethylamine (0.22 mL; 1.59 mmol). The mixture was cooled in an ice bath and isobutylchloroformate (0.11 mL; 0.87 mmol) was added dropwise. After stirring for 2.5 hr in the ice bath, a portion of the reaction mixture (⅓) was removed. To the remaining reaction mixture was added 4-(trifluoromethyl)aniline (0.11 g; 0.69 mmol). The reaction mixture was allowed to warm to room temperature and then was heated at 50-60° C. for 5 hr. The mixture was allowed to cool to room temperature and then extracted with methylene chloride and phosphate buffer (pH=5-6). The methylene chloride layer was washed 3 times with phosphate buffer (pH=5-6), dried over sodium sulfate, filtered and concentrated in vacuo. The residue was dissolved in methanol, and treated with 0.5 mL of 0.5 M NaOH at room temperature for 1.5 hr. The pH of the reaction mixture was then adjusted to 7 with phosphate buffer and extracted with methylene chloride. The aqueous layer was extracted 2 times with methylene chloride, and the methylene chloride layers were combined, dried over sodium sulfate, and concentrated onto a plug of silica gel. The silica gel plug was added to a column of 20 mL of silica gel and the product eluted with methylene chloride. The desired fractions were combined and concentrated in vacuo. The solids were purified on silica gel (20-30% ethyl acetate/hexane). Fractions containing the desired material (Rf=0.08, 20% ethyl acetate//hexane) were combined and concentrated to give the title compound as a white solid. $^1$H NMR (400 MHz, DMSO-$d_6$) δ 11.3 (br s, 1H), 8.05-8.07 (br s, 1H), 7.96 (br d, J=8.00 Hz, 3H), 7.76 (d, J=8.69 Hz, 2H). MS (ESI+) m/z=408, 410 (3:1) (M+1); MS (ESI− m/z=406, 408 (3:1) (M−1)

Example 8. Commercial Compounds

The following known compounds were purchased from commercial sources:

| compound | Structure and name |
| --- | --- |
| 10 | 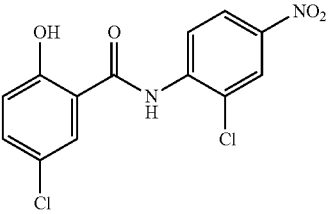5-chloro-N-(2-chloro-4-nitrophenyl)-2-hydroxybenzamide (niclosamide) |
| 11 | 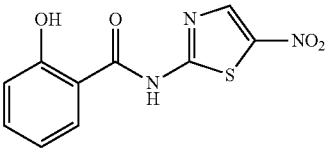2-hydroxy-N-(5-nitrothiazol-2-yl)benzamide (tizoxanide) |
| 12 | 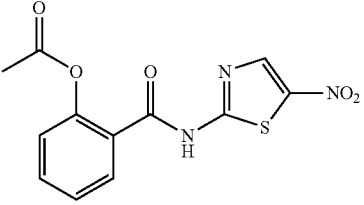2-((5-nitrothiazol-2-yl)carbamoyl)phenyl acetate (nitazoxanide) |
| 13 | 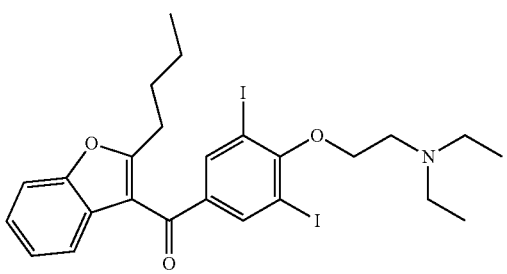(2-butylbenzofuran-3-yl)(4-(2-(diethylamino)ethoxy)-3,5-diiodophenyl)methanone (amiadarone) |

| compound | Structure and name |
|---|---|
| 14 | 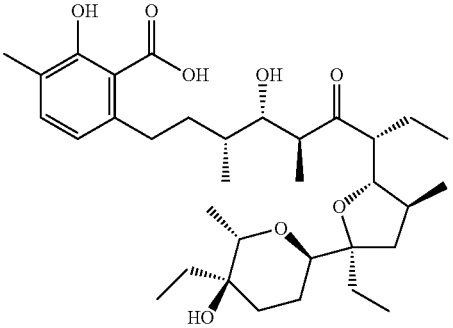
6-((3R,4S,5S,7R)-7-((2S,3S,5S)-5-ethyl-5-((2R,5R,6S)-5-ethyl-5-hydroxy-6-methyltetrahydro-2H-pyran-2-yl)-3-methyltetrahydrofuran-2-yl)-4-hydroxy-3,5-dimethyl-6-oxononyl)-2-hydroxy-3-methylbenzoic acid (lasalocid) |
| 15 | 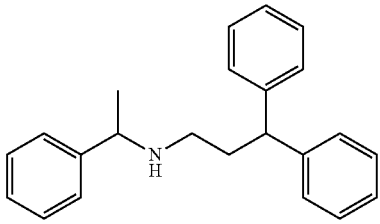
3,3-diphenyl-N-(1-phenylethyl)propan-1-amine (fendiline) |
| 16 | 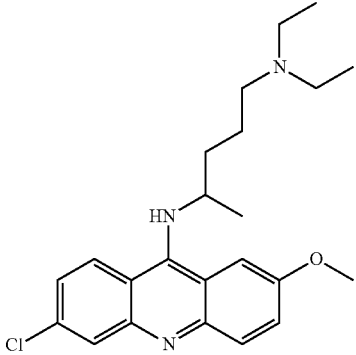
$N^4$-(6-chloro-2-methoxyacridin-9-yl)-$N^1$,$N^1$-diethylpentane-1,4-diamine (quinacrine) |

| compound | Structure and name |
|---|---|
| 17 | 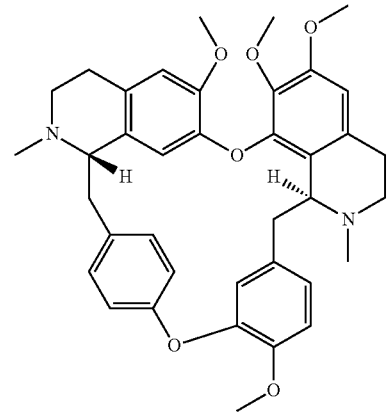<br>($1^1S,3^1S$)-$1^6,3^6,3^7,5^4$,tetramethoxy-$1^2,3^2$-dimethyl-$1^1,1^2,1^3,1^4,3^1,3^2,3^3,3^4$,octahydro-2,6-dioxa-1(7,1),3(8,1)-diisoquinolina-5(1,3),7(1,4)-dibenzenacyclooctaphane<br>(tetrandrine) |
| 18 | 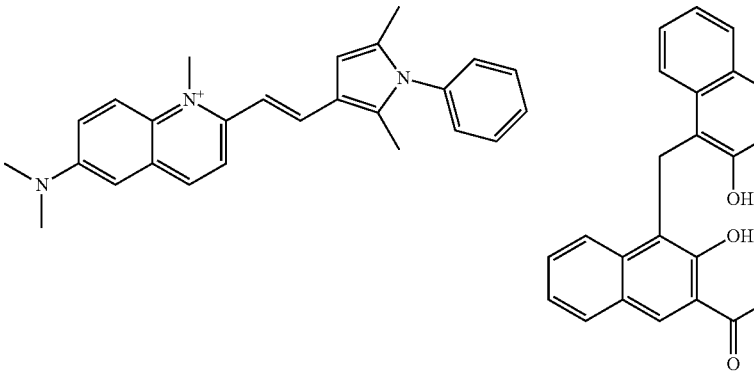<br>2-[(E)-2-(2,5-Dimethyl-1-phenylpyrrol-3-yl)ethenyl]-N,N,1-trimethylquinolin-1-ium-6-amine pamoate<br>(pyrvinium pamoate) |
| 19 | 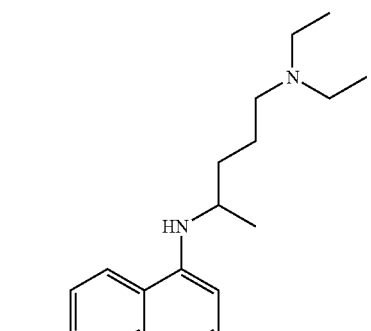<br>$N^4$-(7-chloroquinolin-4-yl)-$N^1,N^1$-diethylpentane-1,4-diamine<br>(chloroquine) |

Example 9. In Vitro Biological Activity

A. Internalization Assay (PD1-GFP)

U2OS cells were transfected with PD1-GFP and stable receptor-expressing cells were selected using 0.5 mg/ml Geneticin in the culture medium. The stable cells were split into glass bottom 384-well plates (MGB 101-1-2-LG, MatriCal, Spokane, Wash.) at a density of 6000 cells/25 μL of medium per well using a Multidrop 384 dispenser (Titertek Instruments, Huntsville, Ala.). The plates were incubated overnight at 37° C. in 5% CO2. The following day, chemical compounds (10 mM in DMSO) were diluted 1:200 in culture medium, 6.25 μL of which was then added to each well of cells to produce a 1:1000 dilution overall and final compound concentration of 10 μM per well. The cells were incubated with compound for 6 h at 37° C. prior to fixation in PBS containing 0.5% paraformaldehyde for 30 min at room temperature. The wells were then washed with PBS three times and stored at 4° C. The cells were imaged using a Zeiss LSM-510 confocal microscope.

B. Western Blot Analysis

Murine breast cancer cells were grown in DMEM medium supplemented with 10% FBS and penicillin and streptomycin antibiotics at 37° C. in 5% CO2.

Figure 2:
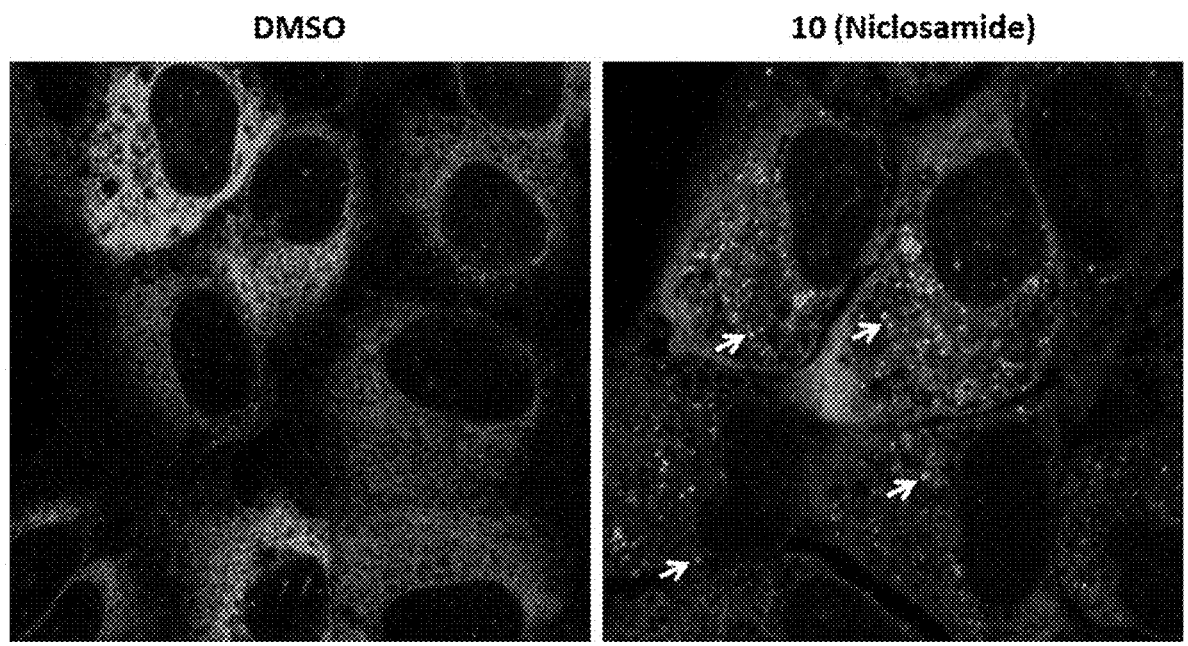
FIG. 2 shows confocal images of PDL1-GFP stable U2OS cells treated with DMSO control or niclosamide (10 μM) for 6 h at 37° C. Punctuate structures (white arrows) highlight aggregated PDL1-GFP vesicles.
Figure 3:
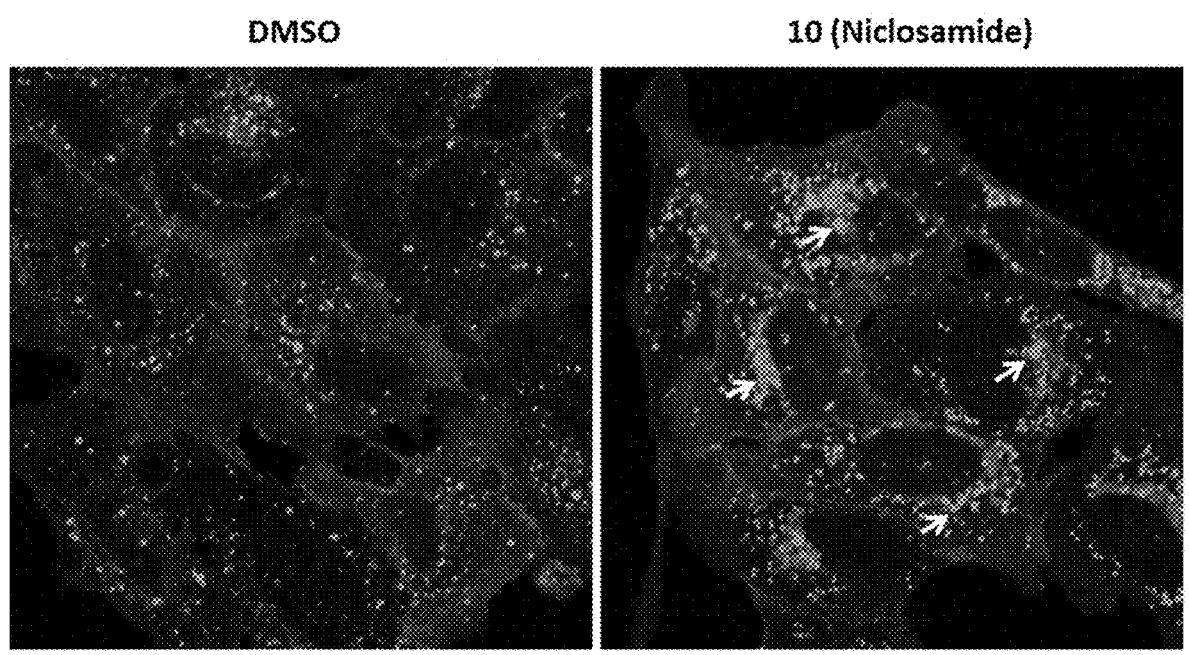
FIG. 3 shows confocal images of CTLA4-GFP stable U2OS cells treated with DMSO control or niclosamide (10 μM) for 6 h at 37° C. White arrows highlight aggregated CTLA4-GFP vesicles.
Figure 4:
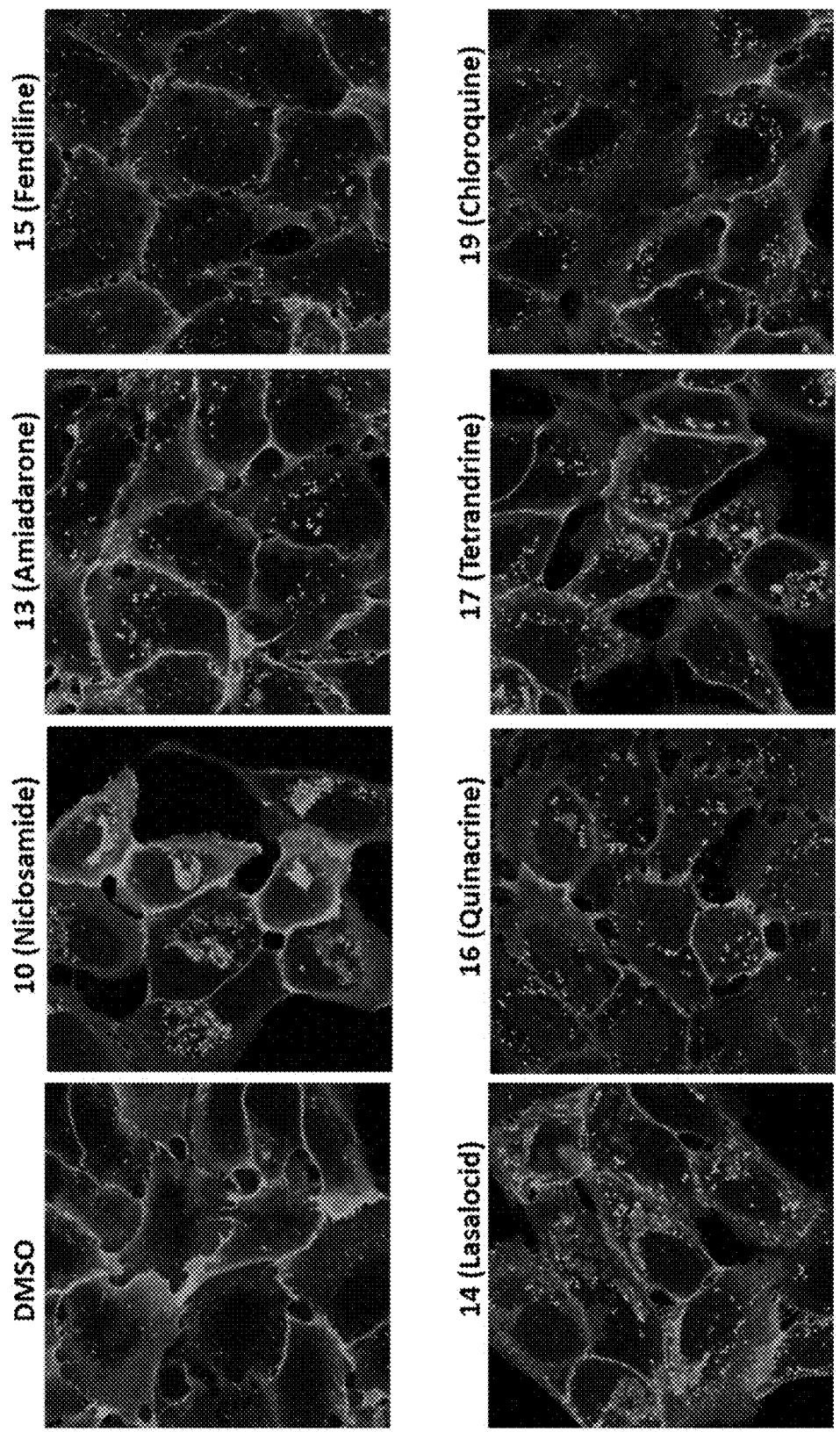
FIG. 4 shows confocal images of PD1-GFP stable U2OS cells treated with DMSO control or exemplary compounds at 10 μM for 6 h at 37° C.
Figure 5:
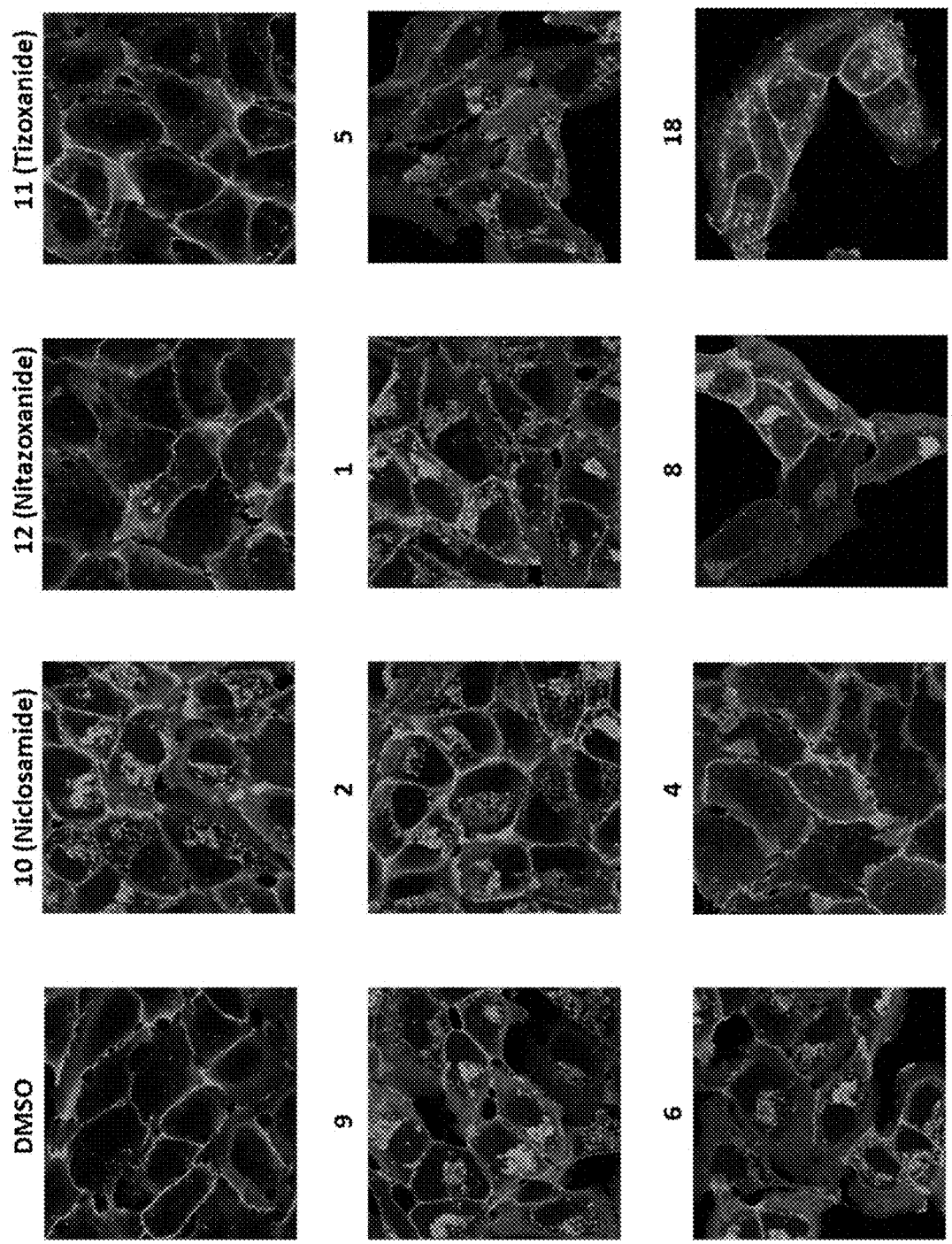
FIG. 5 shows confocal images of PD1-GFP stable U2OS cells treated with DMSO control or exemplary compounds at 10 μM for 6 h at 37° C.
Figure 6:
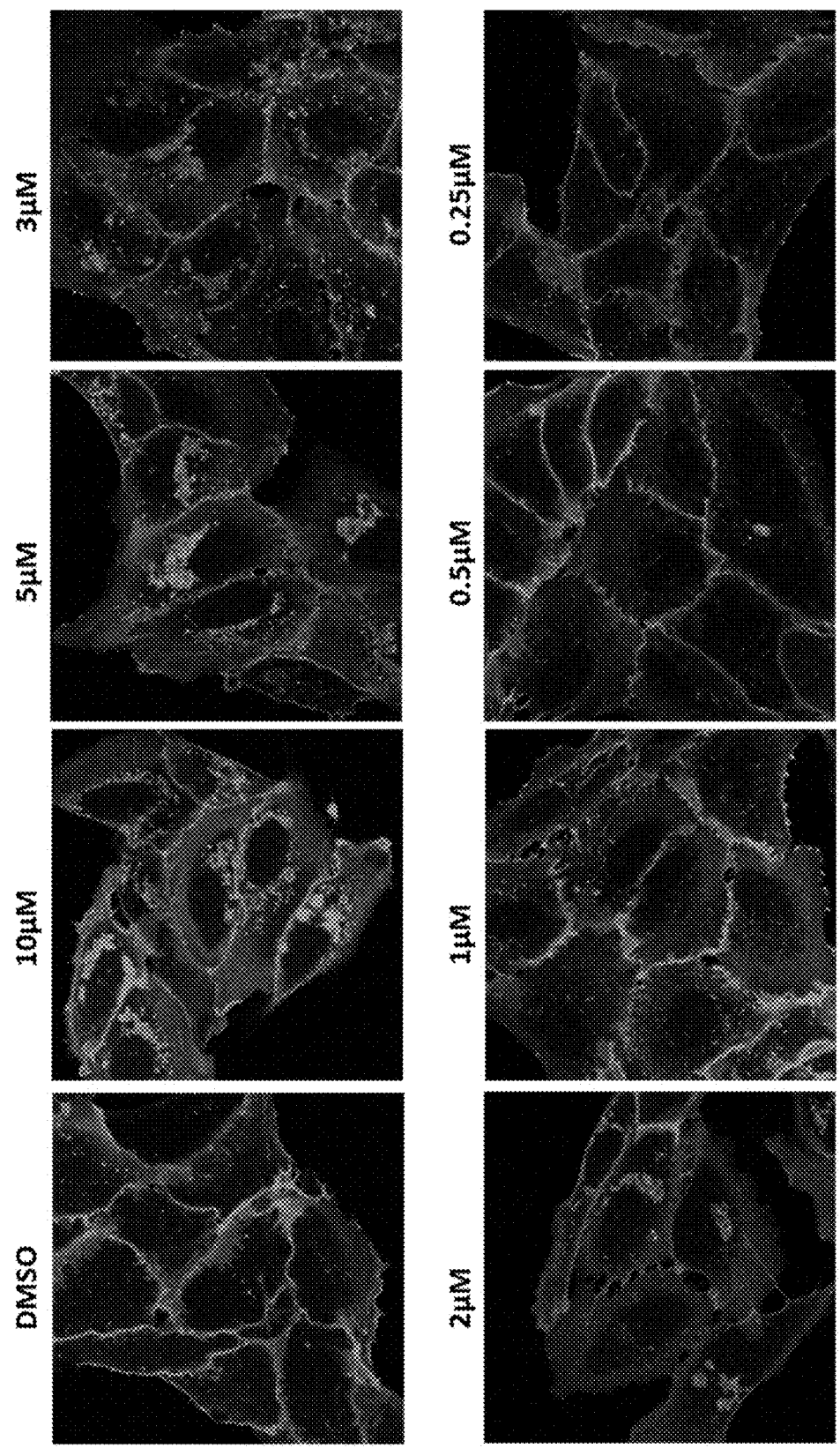
FIG. 6 shows confocal images of PD1-GFP stable U2OS cells treated with DMSO control or niclosamide (0.25 μM to 10 μM) for 6 h at 37° C.
Figure 7:
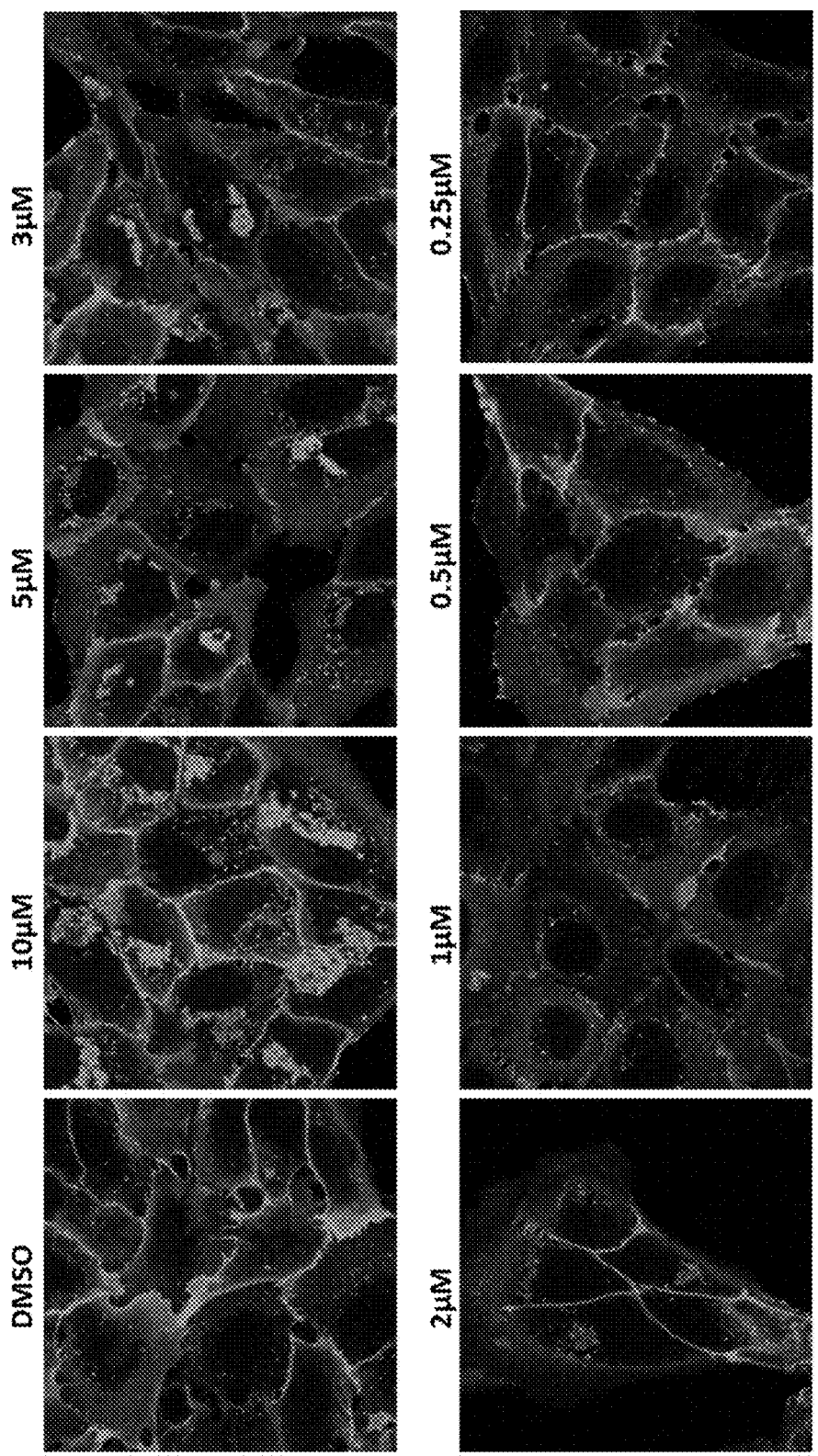
FIG. 7 shows confocal images of PD1-GFP stable U2OS cells treated with DMSO control or compound 7 (0.25 μM to 10 μM) for 6 h at 37° C.
Figure 8:
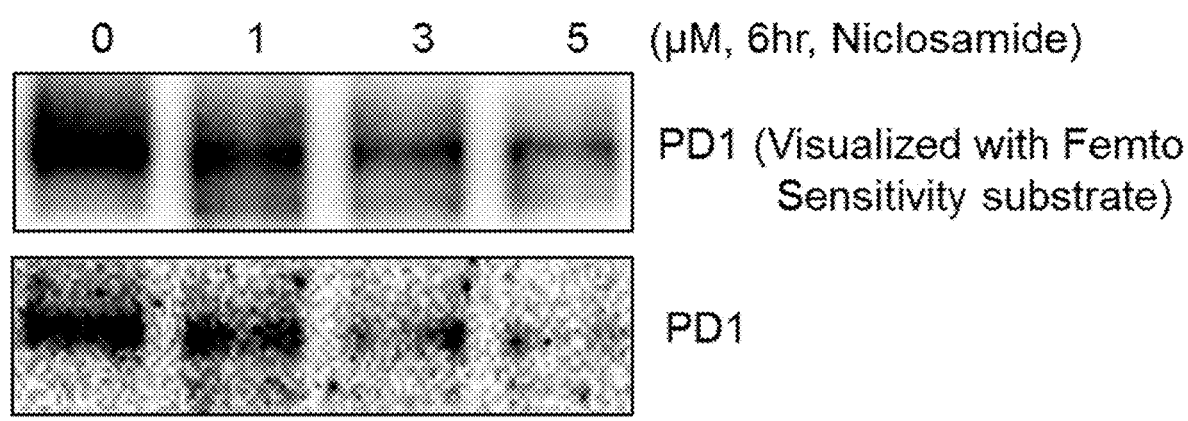
FIG. 8 is a western blot analysis showing that niclosamide decreases PD-1 protein levels at 6 hours. 4T1 Murine breast cancer cells stably expressing PD-1 were treated with Niclosamide at the indicated concentration for 6 hrs. Cells were lysed with SDS sample buffer and lysates were analyzed by western blot.
Figure 9:
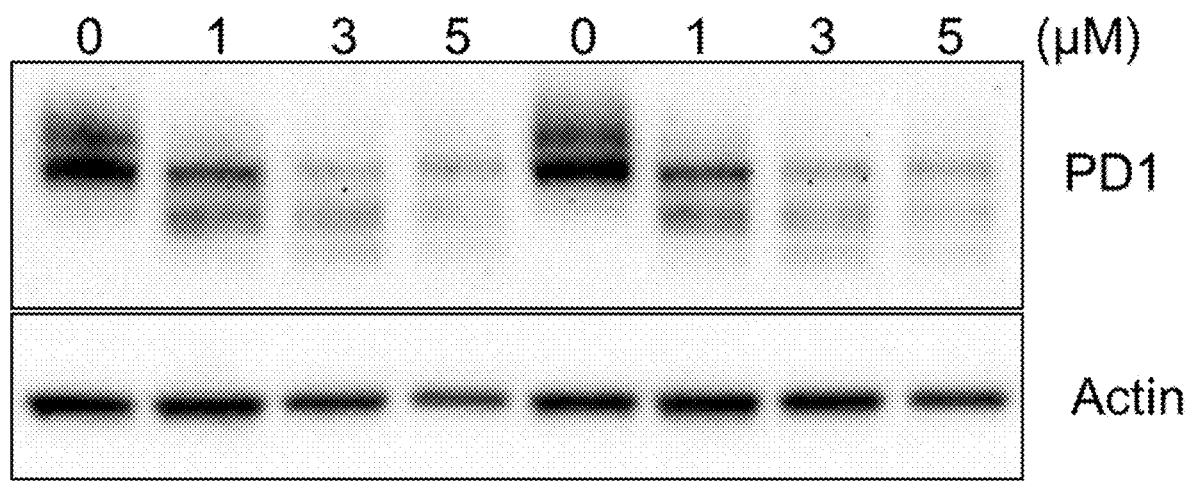
FIG. 9 is a western blot analysis showing that niclosamide decreases PD-1 protein levels at 24 hours. 4T1 Murine breast cancer cells stably expressing PD-1 were treated with niclosamide at the indicated concentration for 24 hrs. Cells were lysed with SDS sample buffer and lysates were analyzed by western blot.
Figure 10:
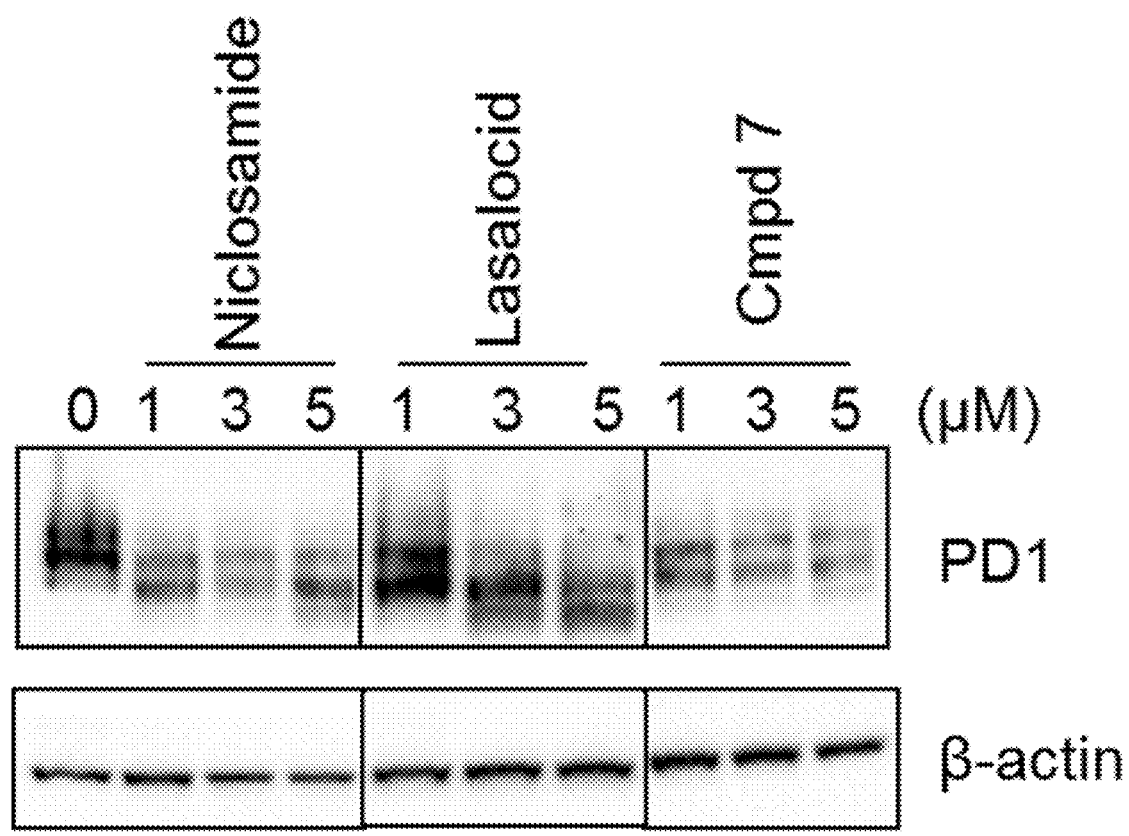
FIG. 10 is a western blot analysis showing that niclosamide, lasalocid and compound 7 lower PD-1 protein levels. 4T1 Murine breast cancer cells (30 k cells/per well in 12-well plates) stably expressing PD-1 were treated with compounds at the indicated concentration for 24 hrs. Cells were lysed with SDS sample buffer and lysates were analyzed by western blot.
Figure 11:
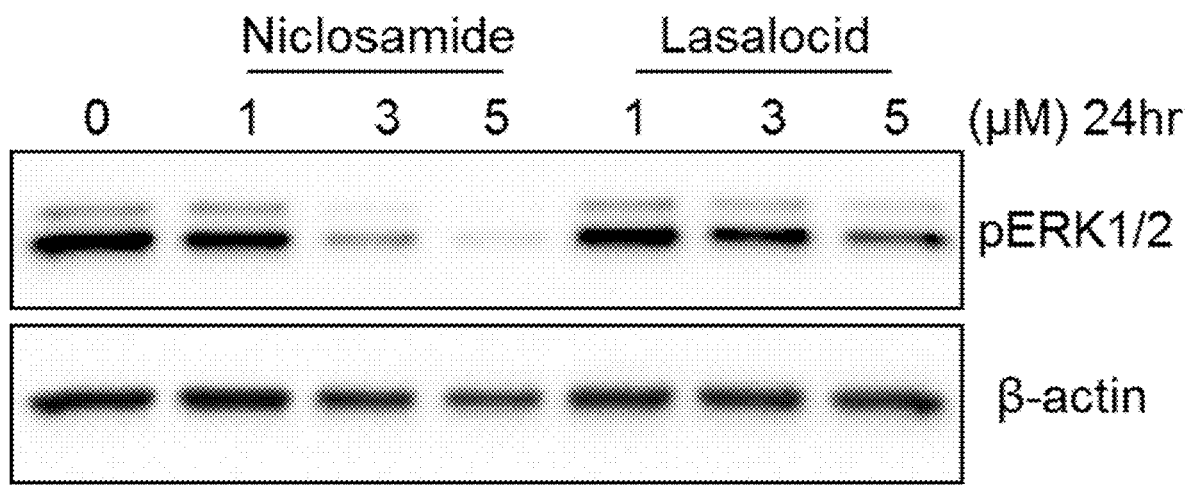
FIG. 11 is a western blot analysis showing that niclosamide and lasalocid lower phospho-Erk1/2 levels in 4T1-PD1 cells. 4T1-PD1 cells (30K cells/per well) were seeded in 12-well plates overnight. On the following day, the compounds were added and the cells were incubated for 24 hours. The cells were then lysed in SDS sample buffer and analyzed by western blots.
Figure 12:
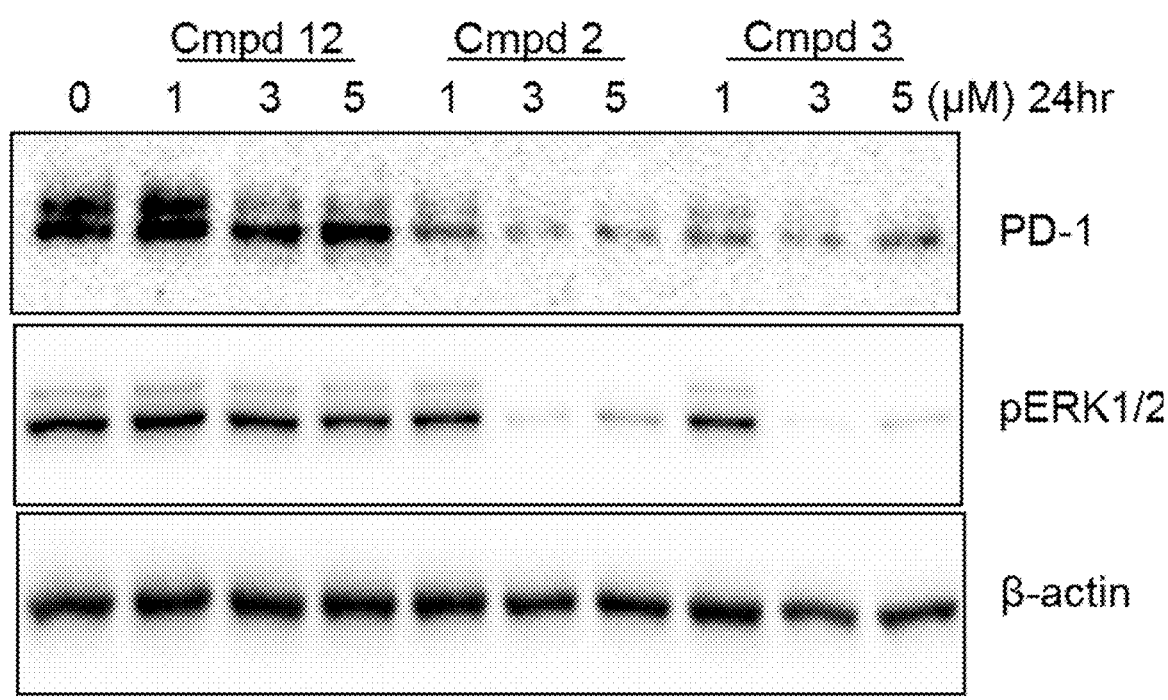
FIG. 12 is a western blot analysis showing that compound 12 (nitazoxanide), compound 2 and compound 3 lower PD-1 and phopho-Erk1/2 protein levels in 4T1-PD1 cells. 4T1-PD1 cells (30K cells/per well) were seeded in 12-well plates overnight. On the following day, the compounds were added and the cells were incubated for 24 hours. The cells were then lysed in SDS sample buffer and analyzed by western blot.
Figure 13:
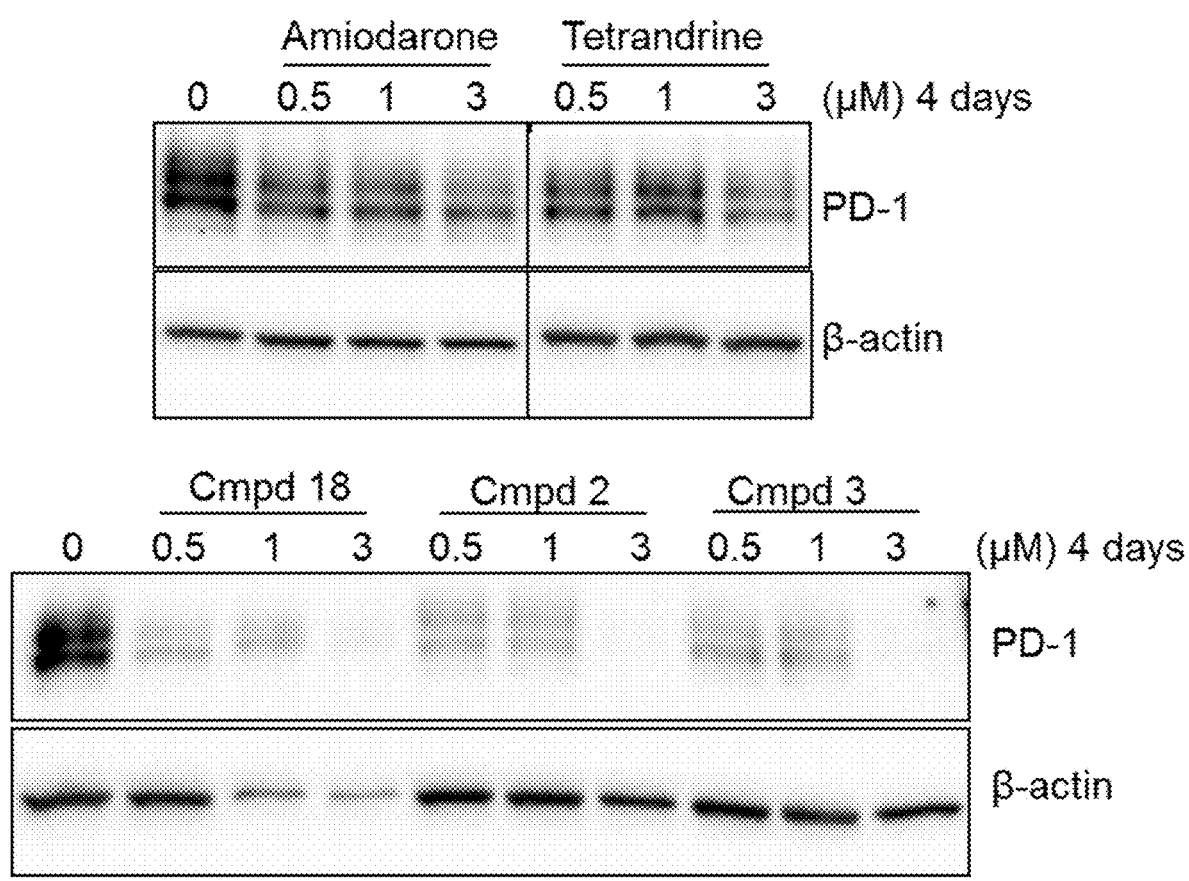
FIG. 13 is a western blot analysis showing that amiodarone, tetrandrine, pyrvinium pamoate, compound 2 and compound 3 lower PD-1 protein levels. 4T1-PD1 cells (10K cells/per well) were seeded in 12-well plates overnight. On the following day, the compounds were added and the cells incubated for 4 days. The cells were then lysed in SDS sample buffer and analyzed by western blot.

4T1 Murine breast cancer cells stably expressing PD1 were seeded in 12-well plates (30 k cells/well) and incubated overnight. On the next day, compounds were added to produce the final concentration desired and the cells were incubated for 12 hours. Cells were lysed with SDS sample buffer and lysates were subjected to western blot analysis 4T1-PD1 cells were seeded in 12-well plates (100 k cells/well) overnight. On the next day, compounds were added and the cells incubated for 4 days. The cells were then lysed in SDS sample buffer and lysates were subjected to western blot analysis C. Results and Discussion of In Vitro Biological Activity Data The results of the PD1-GFP and western blot analyses are shown in Table 1. The data in Table 1 and FIG. 1-7 demonstrates that the disclosed compounds down-regulate PD1 and CTLA-4 as evidenced by the internalization of PD1-GFP and CTLA4-GFP. Compounds in Table 1 that promoted the greatest internalization are represented with 4 + symbols. Western blot analyses in Table 1 and FIG. 8-13 demonstrate that the compounds decrease PD-1 protein levels. Compounds in Table 1 that show the greatest decrease in PD-1 levels are represented with 3 + symbols.

TABLE 1

| Compound | Internalized PD1-GFP punctate; 6 hr (10 μM)* | Internalized CTLA4-GFP punctate; 6 hr (10 μM)** | Decrease in PD1 protein level by western blot at 24 h at 5 μM † | Decrease in PD1 protein level by western blot at 4 days at 3 μM ‡ |
|---|---|---|---|---|
| DMSO | + | + | | |
| 1 | ++++ | | | |
| 2 | ++++ | | ++ | +++ |
| 3 | | | ++ | +++ |
| 4 | ++ | | | |
| 5 | ++++ | | | |
| 6 | ++++ ++++ | | | |
| 7 | (EC$_{50}$ = 3 μM; see FIG. 7) | | ++ | |
| 8 | ++++ | | | |
| 9 | ++++ ++++ | | | |
| 10 | (EC$_{50}$ = 3 μM; see FIG. 6) | +++ | +++ | |
| 11 | ++ | | | |
| 12 | ++ | | + | |
| 13 | +++ | | | ++ |
| 14 | ++++ | | ++ | |
| 15 | ++ | | | |
| 16 | +++ | | | |
| 17 | +++ | | | ++ |
| 18 | ++++ | | | +++ |
| 19 | +++ | | | |

*4+ Scale with + least and ++++ most;
**4+ Scale with + least and ++++ most;
† 3+ Scale with + least and +++ most;
‡ 3+ Scale with + least and +++ most It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound selected from the group consisting of:
4-fluoro-2-(5-nitro-1H-benzo[d]imidazol-2-yl)phenol;
6-chloro-2-(trifluoromethyl)-N-(4-(trifluoromethyl)phenyl)-1H-benzo[d]imidazole-4-carboxamide; and
4-chloro-2-(5-(4-nitrophenyl)-4H-1,2,4-triazol-3-yl)phenol,
or a pharmaceutically acceptable salt thereof.

2. A pharmaceutical composition comprising at least one pharmaceutically acceptable carrier and an effective amount of a compound of claim 1 or a pharmaceutically acceptable salt thereof.

3. The compound of claim 1, wherein the compound is 6-chloro-2-(trifluoromethyl)-N-(4-(trifluoromethyl)phenyl)-1H-benzo[d]imidazole-4-carboxamide, or a pharmaceutically acceptable salt thereof.

4. The pharmaceutical composition of claim 2, wherein the compound is 6-chloro-2-(trifluoromethyl)-N-(4-(trifluoromethyl)phenyl)-1H-benzo[d]imidazole-4-carboxamide, or a pharmaceutically acceptable salt thereof.

* * * * *